(12) United States Patent
Sano et al.

(10) Patent No.: US 10,963,805 B2
(45) Date of Patent: Mar. 30, 2021

(54) REGRESSION ANALYSIS SYSTEM AND REGRESSION ANALYSIS METHOD THAT PERFORM DISCRIMINATION AND REGRESSION SIMULTANEOUSLY

(71) Applicant: MAXELL, LTD., Kyoto (JP)

(72) Inventors: Yuko Sano, Tokyo (JP); Akihiko Kandori, Tokyo (JP); Toshinori Miyoshi, Tokyo (JP)

(73) Assignee: MAXELL, LTD., Kyoto (JP)

( * ) Notice: Subject to any disclaimer, the term of this patent is extended or adjusted under 35 U.S.C. 154(b) by 787 days.

(21) Appl. No.: 14/358,369

(22) PCT Filed: Oct. 5, 2012

(86) PCT No.: PCT/JP2012/075889
§ 371 (c)(1),
(2) Date: May 15, 2014

(87) PCT Pub. No.: WO2013/077093
PCT Pub. Date: May 30, 2013

(65) Prior Publication Data
US 2014/0304213 A1    Oct. 9, 2014

(30) Foreign Application Priority Data

Nov. 21, 2011 (JP) .................... 2011-253439

(51) Int. Cl.
*G06N 7/00* (2006.01)
*G16H 50/70* (2018.01)
*G06K 9/62* (2006.01)
*G06F 17/18* (2006.01)
*G06N 20/00* (2019.01)

(52) U.S. Cl.
CPC ............. *G06N 7/005* (2013.01); *G06F 17/18* (2013.01); *G06K 9/6269* (2013.01); *G06N 20/00* (2019.01); *G16H 50/70* (2018.01)

(58) Field of Classification Search
CPC .................................................. G06N 99/005
See application file for complete search history.

(56) References Cited

PUBLICATIONS

E. Frank et al., "Technical Note: Using Model Trees for Classification", in Machine Learning, vol. 32, 1998, pp. 63-76.*
A. Smola and B. Scholkopf, "A tutorial on support vector regression", Stat. and Computing, vol. 14, 2004, pp. 199-222.*

(Continued)

*Primary Examiner* — Vincent Gonzales
(74) *Attorney, Agent, or Firm* — Mattingly & Malur, PC

(57) ABSTRACT

The present invention solves a problem that there may be a case that an estimated value of regression cannot be calculated depending on a discrimination result when a regression method is applied after a discrimination method, and has a purpose to obtain an estimating equation with high accuracy even when the number of sample groups to which the regression method is applied is small. An estimating equation that satisfies the regression and discrimination at the same time can be obtained by combining a discrimination evaluation function that evaluates discrimination accuracy and a regression evaluation function that evaluates regression accuracy, calculating a combination evaluation function, and optimizing the combination evaluation function.

15 Claims, 16 Drawing Sheets

(56) References Cited

PUBLICATIONS

S. Bibi et al., "Software defect prediciton using regression via classificaiton", AICCSA 2006, 7 pages.*
M. Bilenko and R. Mooney, "Adaptive Duplicate Detection Using Learnable String Similarity Measures", SIGKDD 2003, pp. 39-48.*
B. Bhanu, "Automatic Target Recognition: State of the Art Survey", IEEE Trans. on Aerospace and Elec. Sys., vol. AES-22, No. 4, Jul. 1986, pp. 364-379.*

* cited by examiner

FIG. 8

(a) SAMPLE GROUP

| | CHARACTERISTIC AMOUNT 1 | CHARACTERISTIC AMOUNT 2 | ... | CHARACTERISTIC AMOUNT p | EVALUATION VALUE | |
|---|---|---|---|---|---|---|
| SAMPLE 1 (UNIMPAIRED PERSON) | * | * | ... | * | — | ⎫ WITHOUT EVALUATION VALUE |
| ... | ... | ... | | ... | ... | |
| SAMPLE M (UNIMPAIRED PERSON) | * | * | ... | * | — | ⎭ |
| SAMPLE M+1 (PD PATIENT) | * | * | ... | * | * | ⎫ WITH EVALUATION VALUE |
| ... | ... | ... | | ... | ... | |
| SAMPLE N (PD PATIENT) | * | * | ... | * | * | ⎭ |

(b) NEW SAMPLE

| | CHARACTERISTIC AMOUNT 1 | CHARACTERISTIC AMOUNT 2 | ... | CHARACTERISTIC AMOUNT p | EVALUATION VALUE |
|---|---|---|---|---|---|
| NEW SAMPLE (EXISTENCE OF DISORDER AND ITS SEVERITY ARE UNKNOWN) | * | * | ... | * | UNKNOWN |

*: REPRESENTING A NUMERICAL VALUE

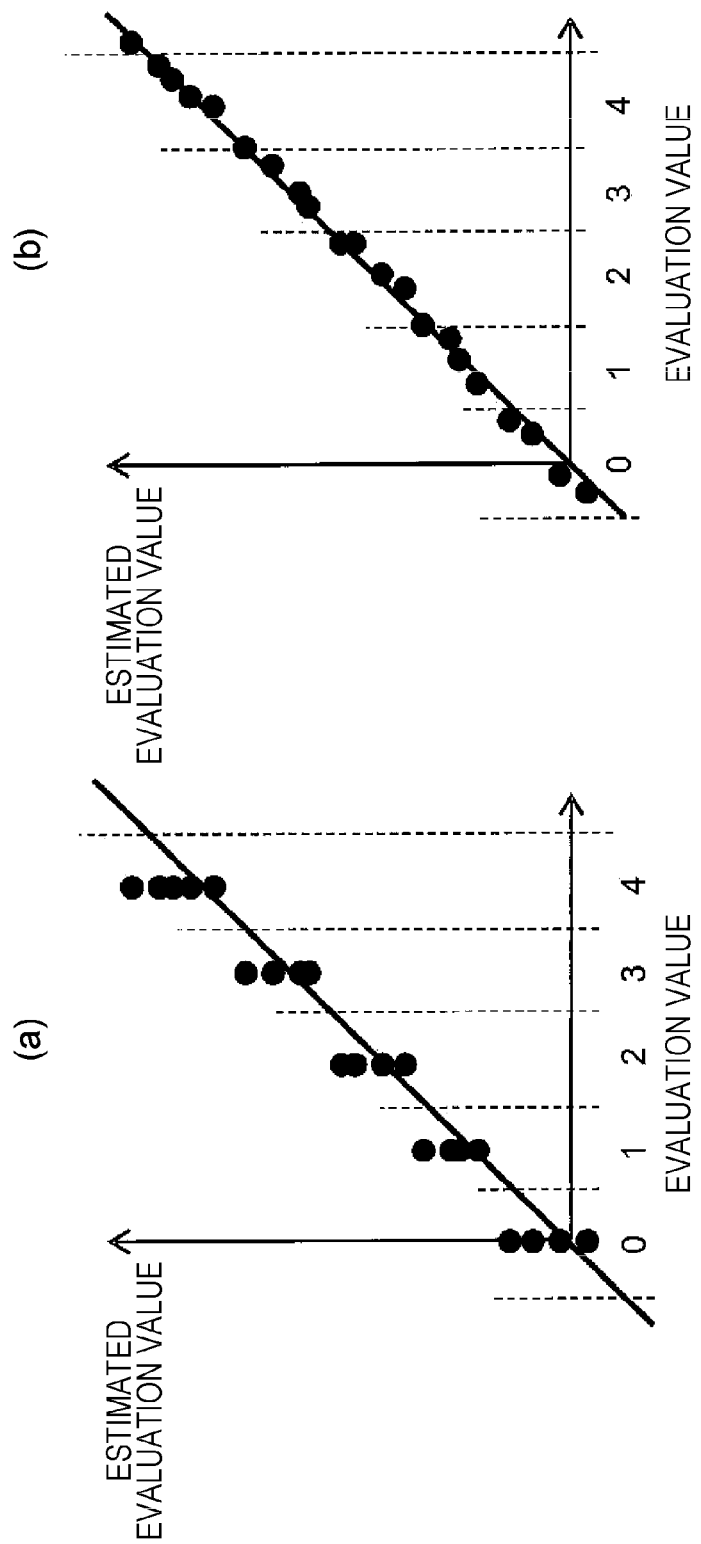

REGRESSION ANALYSIS SYSTEM AND REGRESSION ANALYSIS METHOD THAT PERFORM DISCRIMINATION AND REGRESSION SIMULTANEOUSLY

TECHNICAL FIELD

The present invention relates to a regression analysis system and a regression analysis method for estimating an evaluation value based on a characteristic amount of a new sample with high accuracy by using a characteristic amount and an evaluation value of a sample group.

BACKGROUND ART

Recently, a technology for estimating an evaluation value from a characteristic amount calculated from data of a sample (regression analysis) has become more important in various industrial fields. Taking a medical field as an example, when it is possible to automatically estimate an evaluation scale which expresses a severity of disorder from medical data (images of fMRI or CT, body movement information, etc.) of a subject, it is useful as a screening test performed before a doctor makes a diagnosis. As another example, in a field of production management, it is considered a case that a level of defection is evaluated from an examination images of a product (e.g., a semiconductor component) and a highly reliable component is selected. In addition, as a traffic accident prevention system, a possibility of crashing to an object is estimated based on an image of a vehicle-mounted camera and, when the crash possibility is high, brake is applied. Hereinafter, it will be explained taking the medical field as an example.

As described above, an algorism for estimating an evaluation value from a characteristic amount of a sample has following two steps (1) and (2) in general. In step (1), using a discrimination method, a standard to discriminate an evaluation value estimable group (a) and an evaluation value inestimable group (b). Next, in step (2), targeting the sample discriminated as the group (a) in step (1), a standard for estimating an evaluation value from a characteristic amount is obtained by using a regression method. After that, the discrimination standard of step (1) is applied to a new sample to discriminate groups and, only when it is discriminated as group (a), an evaluation value is estimated in step (2).

The above process is performed as follows in the medical field. In step (1), a discrimination standard is created by using characteristic amounts of a patient group (group (a)) and an unimpaired group (group (b)), and in step (2), a standard for estimating an evaluation scale from the characteristic amount of the patient group (group (a)) is obtained. After that, regarding a new subject in a case that the existence of disorder or its severity are unknown, the discrimination standard of step (1) is applied to discriminate it as unimpaired group or patient group, and, only when it is discriminated as a patient group, the evaluation scale is estimated in step (2).

Here, as the discrimination method used in step (1), a linear discrimination analysis, an SVM (Support Vector Machine), and the like are known. As the regression method used in step (2), a multiple regression analysis, an SVM regression, and the like are known.

SUMMARY OF INVENTION

Technical Problem

However, in the algorism that takes two steps in this manner, there are some problems in view of operation and accuracy. In view of operation, there is a problem that, when a new sample is mistakenly discriminated as group (b) in step (1) even though it should be discriminated as group (a), the process does not proceed to step (2) and its evaluation value is not calculated. As explaining in the example of the medical field, there may be a case that, when the discrimination standard of step (1) is applied to data of a new subject whose possibility of disorder is unknown, and it is discriminates as an unimpaired person but a doctor diagnose that there is a possibility of disorder. In this case, there is a problem that, even though the doctor prefers to know an estimated evaluation value, the process does not proceed to step (2) and the evaluation value is not estimated. In addition, there may be a problem that, when the condition transfers from a serious symptom to a mild symptom because of a medical treatment, the evaluation value is estimated while having a serious symptom; however, when the symptom becomes milder, it may be discriminated as the unimpaired group and the evaluation value may not be estimated.

In view of accuracy, there may be a problem that the accuracy of the standards obtained in steps (1) and (2) is lowered since the number of the pieces of data of sample group is small and the accuracy of a final estimated value is further lowered due to the two steps with the low accuracy. In the medical field, due to the absence of data in the patient group, especially, the accuracy of the regression in step (2) is often lowered. It is difficult to collect data of the patient group in a large scale since it is difficult to have an agreement of a patient, it is difficult for busy doctors to examine during diagnosing and treating, the number of patients of the same disorder vising to a hospital is limited, for example.

Solution to Problem

In order to solve the above problem, a new method for simultaneously realizing the discrimination of groups (a) and (b) in step (1) and the evaluating value estimation in step (2) is necessary. In this method, the evaluation values of the groups (a) and (b) are expressed with a unified single index and the discrimination of the groups (a) and (b) is executed by comparing with the index and a threshold value.

Advantageous Effects of Invention

When such a method is realized, there are advantages in view of operation and accuracy.

In view of operation, the problem of the conventional method that the evaluation value cannot be estimated because the process does not proceed to step (2) depending on the discrimination result in step (1). In other words, there is an advantage that an evaluation value can be estimated for any samples. Explaining in the medical field, a problem that the severity cannot be calculated due to an inconsistency between the result of discrimination of the patient group and unimpaired group in step (1) and a doctor's diagnosis dese not occur. Further, since the severity of an unimpaired person and a patient is handled using an unified single index, the manner that the condition of the patient changes from a serious symptom to a mild symptom because of a medical treatment can be followed and observed using the single index.

In view of the accuracy, there is an advantage that the accuracy of estimating an evaluation value by using the data which was separately used in step (1) and step (2) at the same time. In the medical field, lowering of generalizability caused by a lack of data in the patient group can be reduced by using the data of the health group which is easily corrected at the same time.

BRIEF DESCRIPTION OF DRAWINGS

FIGS. 8(a) and 8(b) are diagrams showing configurations of a sample group and a new sample group.

FIGS. 9(a) and 9(b) is pattern diagrams of cases that an evaluation value is assigned to a numerical value distribution.

DESCRIPTION OF EMBODIMENTS

A first configuration for realizing the present invention (hereinafter, referred to as an "embodiment") will be explained in detail with reference to the drawings according to need.

Although the present invention is applicable to data of various industrial fields, the present embodiment is applied to the medical field. The pieces of data to which the present invention is applied in the present embodiment are finger-tapping movement data of an unimpaired group and a Parkinson's disease (PD) patient group and a UPDRS ft score which is an evaluation of severity of the PD patient group. The finger-tapping movement here is a repeated movement that a patient opens and closes their thumb and index finger. The UPDRS ft is an item that evaluates the finger-tapping movement (Finger Tapping) in a UPDRS, which is a value grading a level of the finger-tapping movement. PD is a disease which causes a movement disorder of the entire body and symptoms such astremor, muscle rigidity (stiffness of muscle), bradykinesia (slowness and smallness of movement) remarkably seen in movement of patient's fingers. Doctors visually observes finger-tapping movements of a PD patient and evaluates the movement based on the UPDRS ft.

An outline of the present invention will be explained and a difference from a conventional method will be described. After that, each unit of the present invention will be described. Then, a result of applying the present invention to the above data will be shown.

Principle Units of First Embodiment

Figure 1:
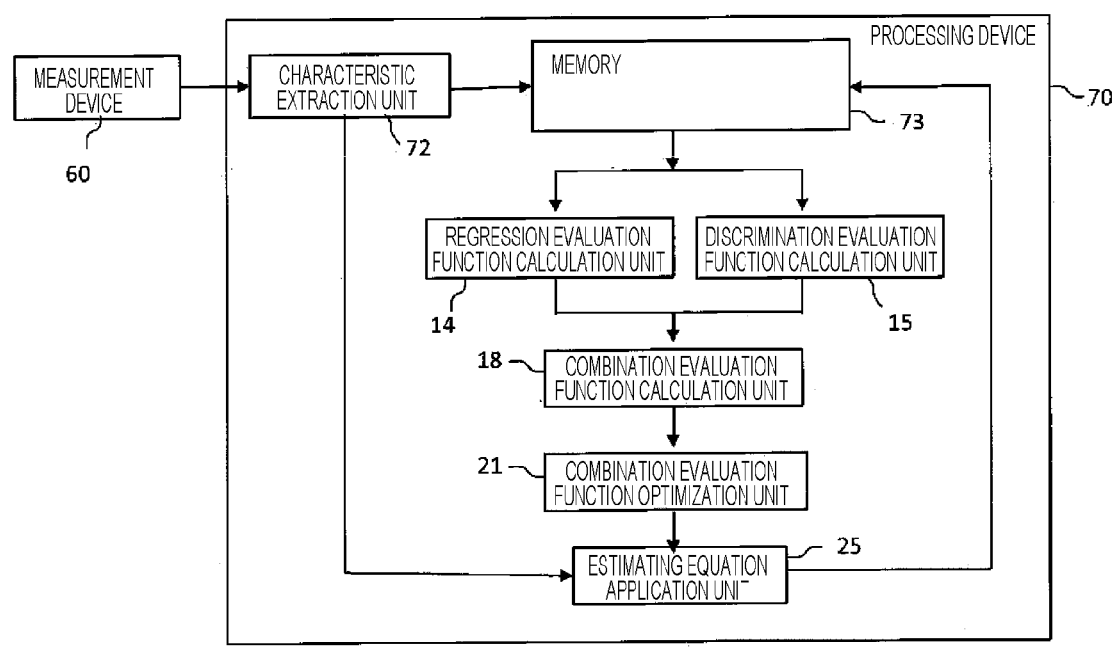
FIG. 1 is a block diagram illustrating a main system configuration of a first embodiment of the present invention.

A system configuration of a first embodiment of the present invention is illustrated in FIG. 1. Measurement target data is measured by a measurement device 60 and imported to a processing device 70. In a characteristic amount extraction device 73, a later described characteristic amount is extracted from imported original data. The characteristic amounts extracted from respective pieces of sample data and evaluation values applied to the sample data are stored in a memory 73. The processing device 70 executes processes to optimize an estimating equation for calculating an estimated evaluation value from a new sample using accumulated values of the special value and evaluation value, and at the same time, to calculate an estimated evaluation value from a characteristic amount of the new sample based on the estimating equation. Here, this process is referred to as a discrimination/regression process.

Figure 2:
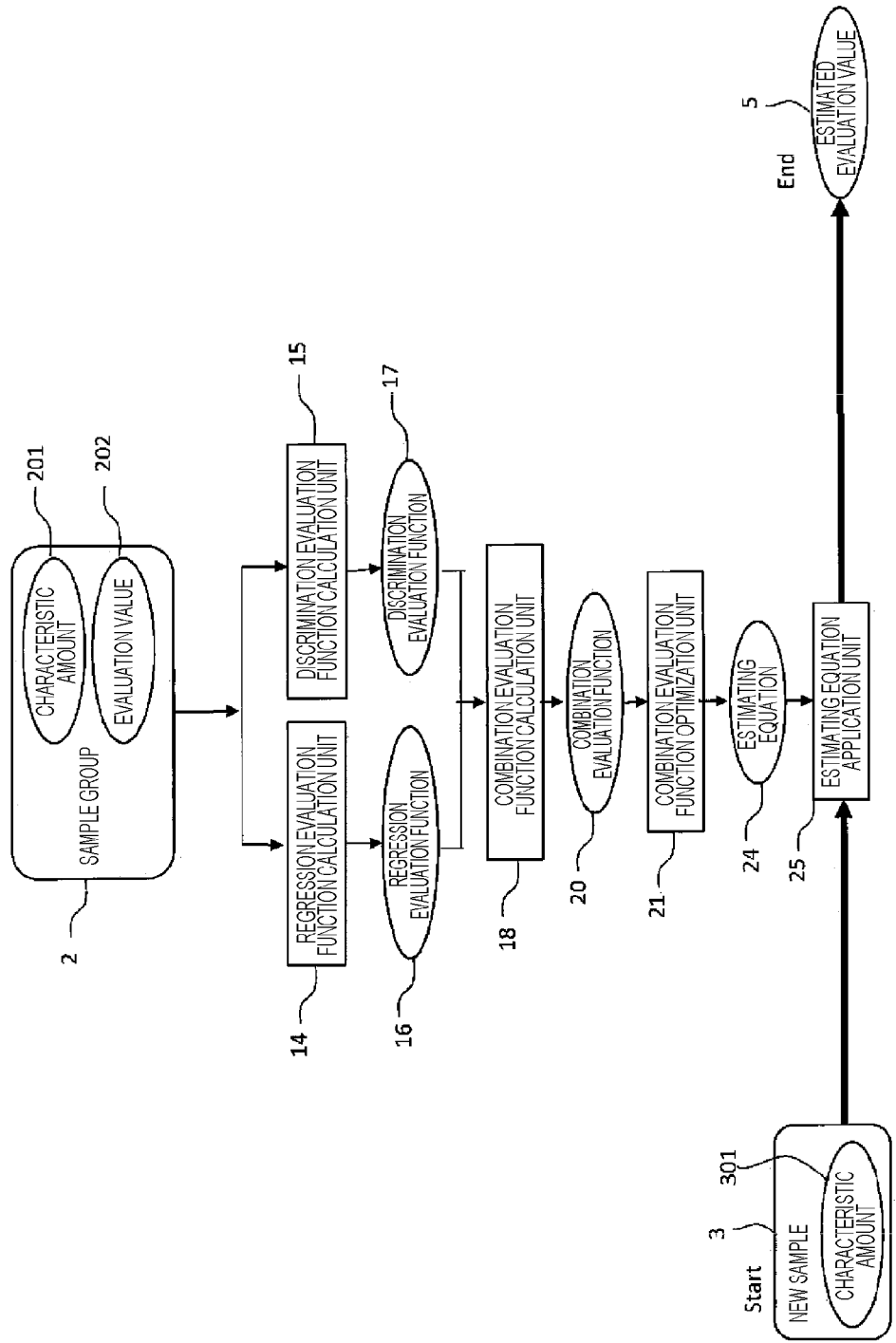
FIG. 2 is a flowchart illustrating a main configuration of a discrimination/regression process of the first embodiment.

FIG. 2 illustrates a flow of the discrimination/regression process. The respective blocks for executing the discrimination/regression process illustrated in FIG. 1 are also represented by the same reference numbers in FIG. 2. Here, the present embodiment will be explained with reference to FIG. 2. Characteristic amounts 201 and evaluation values 202 of (all or a part of) a sample group 2 stored in the memory are introduced to a regression evaluation function calculation unit 14 and the regression evaluation function calculation unit 14 calculates a regression evaluation function 16. In the same manner, the characteristic amounts 201 and evaluation values 202 of (all or a part of) the sample group 2 are introduced to a discrimination evaluation function calculation unit 15 and a discrimination evaluation function 17 is calculated. Then, the regression evaluation function 16 and the discrimination evaluation function 17 are input to the combination evaluation function calculation unit 18 and a combination evaluation function 20 is calculated. Then, a combination evaluation function optimization unit 21 optimizes the combination evaluation function 20 so that an estimating equation 24 is calculated. Then, an estimating equation application unit 25 applies a characteristic amount 301 of a new sample 3 to the estimating equation to calculate an estimated evaluation value 5.

As described above, when discrimination and regression are executed at the same time, two problems of the conventional method are solved. The first problem is that, since a regression process is performed after a discrimination process in the conventional method, an estimation value of the regression is not calculated depending on the discrimination result. According to the first embodiment, since discrimination and regression are performed simultaneously, evaluation values can be estimated for all samples. The second problem is that, in the conventional regression process, the estimation accuracy of the regression process is reduced when the number of samples having a usable evaluation value is small. According to the present invention, since samples lacking a evaluation value can be used in discrimination, the number of usable samples increases and the estimation accuracy is improved.

<<Additional Units to Improve Accuracy>>

Figure 3:
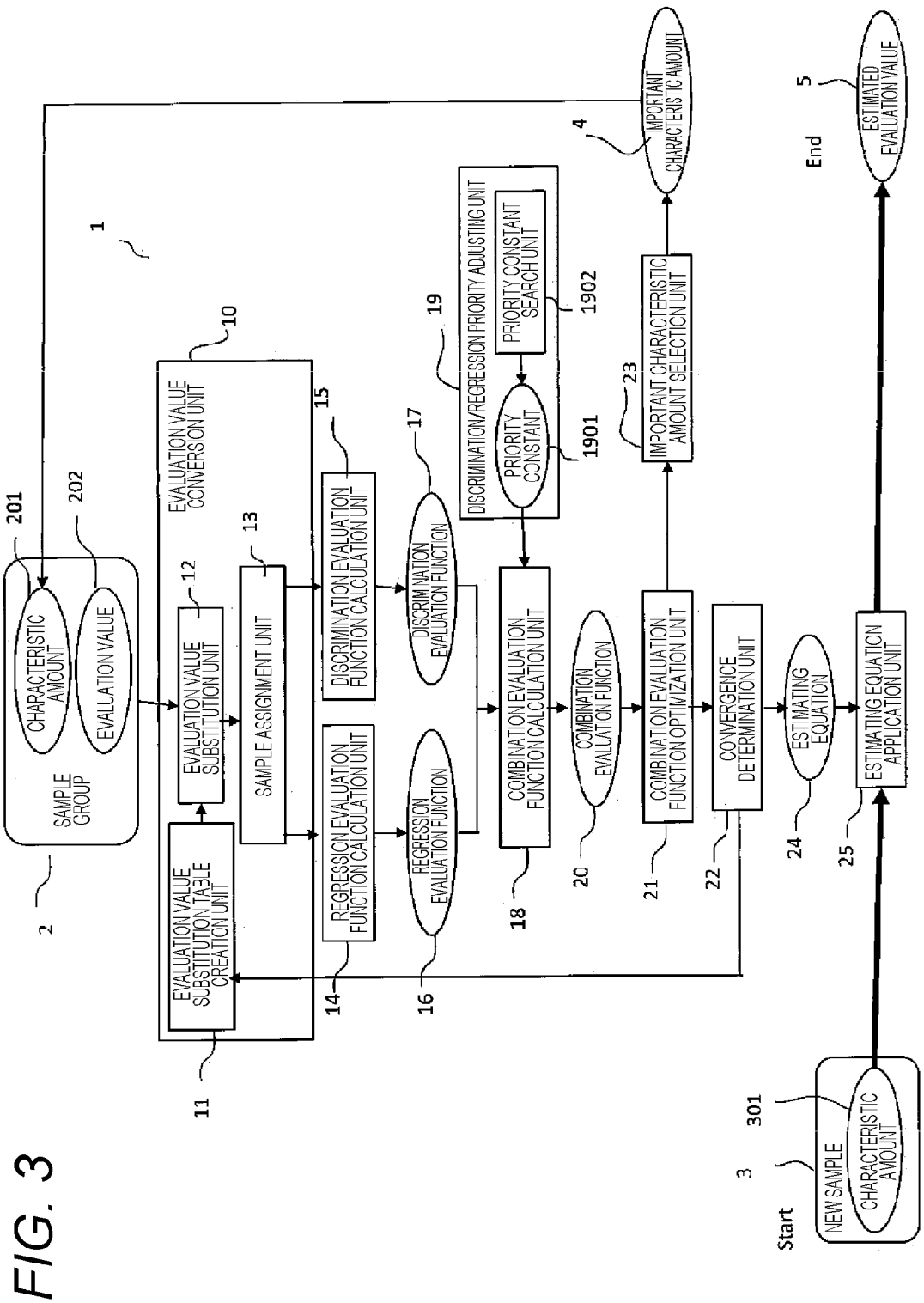
FIG. 3 is a flowchart illustrating a detailed configuration of the discrimination/regression process of the first embodiment.

Further, according to the present embodiment, as illustrated in FIG. 3, by adding following four units to the flow of FIG. 2, the accuracy of the estimating equation can be improved. The four added units are an evaluation value conversion unit 10, a discrimination/regression priority adjusting unit 19, a convergence determination unit 22, and an important characteristic amount selection unit 23. The four units may be separately added to the flow of FIG. 2 or added at once. Hereinafter, configurations and effects of the four units will be explained.

The first evaluation value conversion unit 10 is a unit for converting the evaluation value 202 of the sample group 2 into a numerical value, a numerical value distribution, or a numerical value range before the regression evaluation function calculation unit 14 and discrimination evaluation function calculation unit 15. The evaluation value conversion unit 10 includes an evaluation value substitution table creation unit 11, an evaluation value substitution unit 12, and a sample assignment unit 13. The evaluation value substitution table creation unit 11 creates a table that associates the evaluation value 202 of the sample group 2 with a numerical value, a numerical value distribution, or a numerical value range. This table includes a case of the sample group 2 which lacks the evaluation value 202. The evaluation value substitution unit 12 substitutes the evaluation value 202 of the sample group 2 with a numerical value, a numerical value distribution, or a numerical value range based on the above table. The sample assignment unit 13 assigns the sample of the sample group 2 as a sample input to the regression evaluation function calculation unit 14 and a sample input to the discrimination evaluation function calculation unit 15. Here, there may be a sample to be input to both of the regression evaluation function calculation unit 14 and discrimination evaluation function calculation unit 15.

Effect of the evaluation value conversion unit 10 will be explained. When the evaluation value 202 of the sample group 2 given as a numerical value in advance is converted to a numerical value distribution or a numerical value range, discreteness of the evaluation values can be reduced. Thus, regression and discrimination with an evaluation value that is close to an actual condition can be executed and the accuracy of estimating equation is improved. Further, in a case when the evaluation value is absent, the accuracy of the estimating equation is improved by applying a tentative numerical value, a numerical value range, or a numerical value distribution.

Next, the second discrimination/regression priority adjusting unit 19 will be explained. The discrimination/regression priority adjusting unit 19 is a unit for adjusting priority between the discrimination and regression when the combination evaluation function calculation unit 18 combines the regression evaluation function 16 and the discrimination evaluation function 17. The priority is adjusted based on a magnitude of a priority constant 1901. Here, the priority constant 1901 is a numerical value searched by a priority constant search unit 1902 so as to maximize the accuracy of the estimating equation. Note that the priority constant 1901 may be a predetermined constant.

Effect of the discrimination/regression priority adjusting unit 19 will be explained. Firstly, there is an advantage that the priority can be specified in a case that one of the discrimination and regression needs to be prioritized. Further, the estimation accuracy can be further maximized by using an estimation accuracy of the estimating equation 24 obtained from the combination evaluation function optimization unit 21 in a calculation process in the priority constant search unit 1902.

Next, the third convergence determination unit 22 will be explained. This unit determines whether the optimized result by the combination evaluation function optimization unit 21 sufficiently converges, and when the convergence is not sufficient, feedback is given to the evaluation value substitution table creation unit 11 in the evaluation value conversion unit 10. Based on the feedback, the numerical value, numerical value distribution, or numerical value range used to substitute the evaluation value is corrected. The feedback is continuously given until it is determined that the optimization by the combination evaluation function 20 sufficiently converges.

The effect of the convergence determination unit 22 is that the accuracy of a conclusively-output estimating equation 24 can be improved by correcting the table for substituting the predetermined evaluation value with a numerical value, a numerical value distribution, or a numerical value range based on the result of the combination evaluation function optimization unit 21.

Last of all, the fourth important characteristic amount selection unit 23 will be explained. The important characteristic amount selection unit 23 is a unit for selecting, from the combination evaluation function optimization unit 21, an important characteristic amount that has an influence on the estimation accuracy.

Effect of the important characteristic amount selection unit 23 will be described. It is assumed that, by notifying the important characteristic amount 4 output from the important characteristic amount selection unit 23 to the characteristic amount 201 of the sample group 2 as feedback, data of only the important characteristic amount 4 is selected and the discrimination/regression process is executed again. With this method, multicollinearity which may be caused when there are many characteristic amounts in regression or discrimination can be avoided and the estimation accuracy can be improved. Here, only the important characteristic amount 4 may be output without giving feedback to the characteristic amount 201.

<<Comparison with Conventional Method>>

Figure 4:
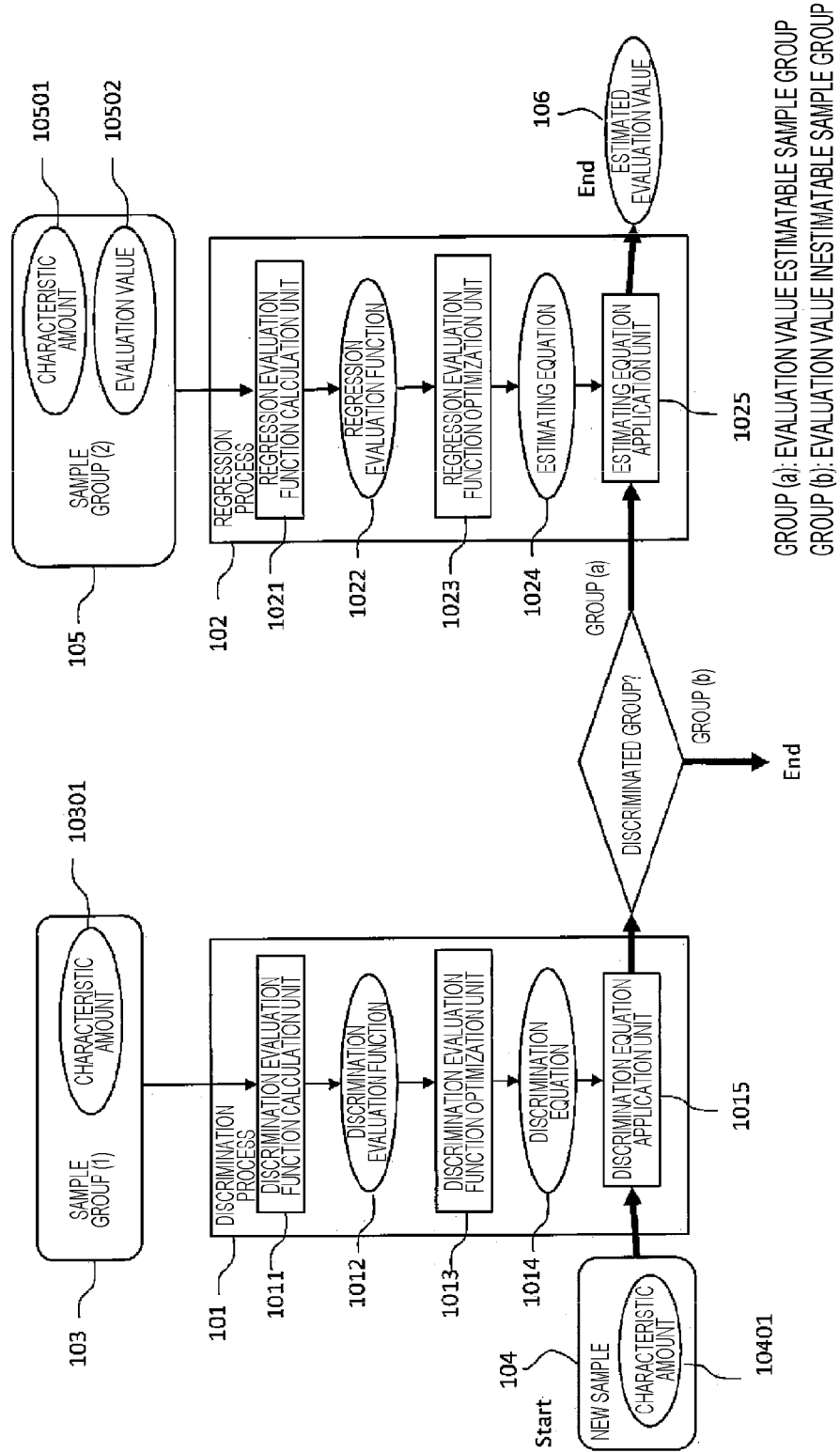
FIG. 4 is a flowchart illustrating a configuration of a conventional method.

Here, referring to a flow of a conventional method illustrated in FIG. 4, a difference from the flow of the present invention will be explained. In the conventional method, after discrimination is executed between an unimpaired group or a patient group in a discrimination process 101 (discrimination analysis and the like), a regression process 102 (multiple regression analysis and the like) is applied and severity is calculated only when it is discriminated as the patient group.

Firstly, the discrimination process 101 is applied to a characteristic amount 10301 of a sample group (1). Inside the discrimination process 101, a discrimination evaluation function calculation unit 1011 calculates a discrimination evaluation function 1012. Then, a discrimination evaluation function 1012 is optimized by a discrimination evaluation function optimization unit 1013 so that a discrimination equation 1014 is calculated.

Next, independently from the discrimination process 101, a regression process is applied to a characteristic amount

10501 and an evaluation value 10502 of a sample group (2). In the regression process 102, the regression evaluation function calculation unit 1021 calculates a regression evaluation function 1022. Then, a regression evaluation function 1022 is optimized by the regression evaluation function optimization unit 1023 so that an estimating equation 1024 is calculated.

Regarding data of a new subject (new sample 104) of a case that the existence of disorder or its severity is unknown, a discrimination equation 1014 is firstly applied by a discrimination equation application unit 1015 and it is discriminated to be in an unimpaired group or a patient group. Next, only when it is discriminated to be a patient group, an estimating equation application unit 1025 applies an estimating equation 1024, and an estimated evaluation value 106 is calculated. In the conventional method, in this manner, the estimated evaluation value 106 is calculated only when the discrimination equation application unit 1015 discriminates as a patient group. In contrast, according to the present invention, an estimated evaluation value 5 (FIG. 2 or FIG. 3) is calculated for every sample.

<<Characteristic Amount and Evaluation Value>>
[Characteristic Amount]

Inputs of the discrimination/regression process according to the present invention are a characteristic amount and an evaluation value. Firstly, a characteristic amount is described.

The characteristic amount is one or more numerical value that is calculated from original data obtained from a sample. Here, original data includes any data such as an image, sound, an electrical voltage, a questionnaire result, and the like as long as data can be expressed by a numerical value. Even category data may be included in original data if it can be expressed by a numerical value. For example, in the medical field, there are a medical image taken by an MRI, a CT or a magnetocardiographic, a waveform measured by an electrocardiograph, a component value of a blood test, a questionnaire for a patient, and the like.

Figure 5:
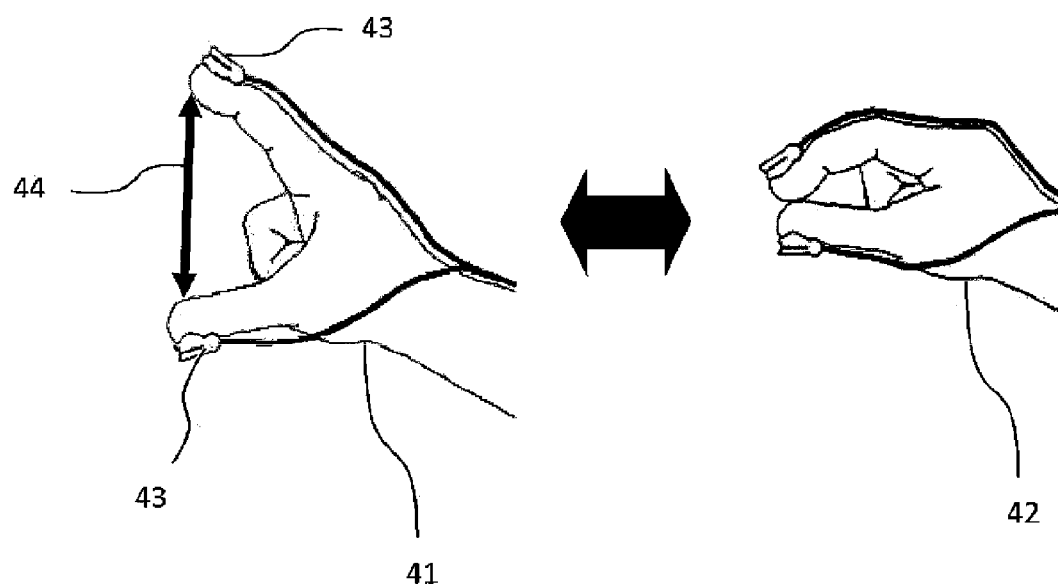
FIG. 5 is a diagram illustrating a finger-tapping movement.

According to the present embodiment, a characteristic amount calculated from finger-tapping movement data is used. The finger-tapping movement is a movement to repeatedly open and close a thumb and an index finger as illustrated in FIG. 5. A state 41 that two fingers are opened and a state 42 that the two fingers are closed are repeated alternately. According to the present embodiment, magnetic sensors 43 are attached to the thumb and index finger respectively and a distance 44 between the two fingers is measured. The magnetic sensor is a sensor including two coils and one of the coil receives a magnetic field generated by the other coil so that a distance between two coils is measured.

Figure 6:
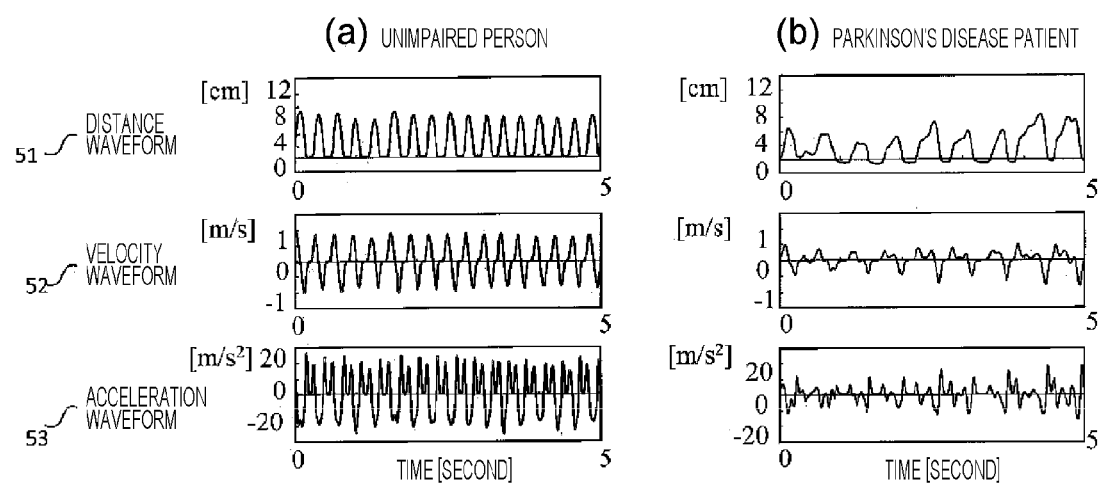
FIGS. 6(a) and 6(b) are waveform diagrams illustrating various waveforms of the finger-tapping movement.

FIG. 6(*a*) illustrates waveforms of typical finger tapping of an unimpaired person; and FIG. 6(*b*) illustrates waveforms of typical finger tapping of a PD patient. A distance waveform 51 is converted from output voltage of the magnetic sensor. By differentiating the distance waveform 51, a velocity waveform 52 and an acceleration waveform 53 are obtained. Based on these waveforms, it is understood that the unimpaired person smoothly repeats the opening and closing movements. On the other hand, it is understood that the PD patient has movements different from those of the unimpaired person due to symptoms such as a stiffness of muscle (muscle rigidity), a rhythm disorder, and the like. Since there are remarkable differences between the finger-tapping movements of the unimpaired person and the PD patient, it is used for doctor's diagnosis by visual observation (UPDRS ft) as described above.

Figure 7:
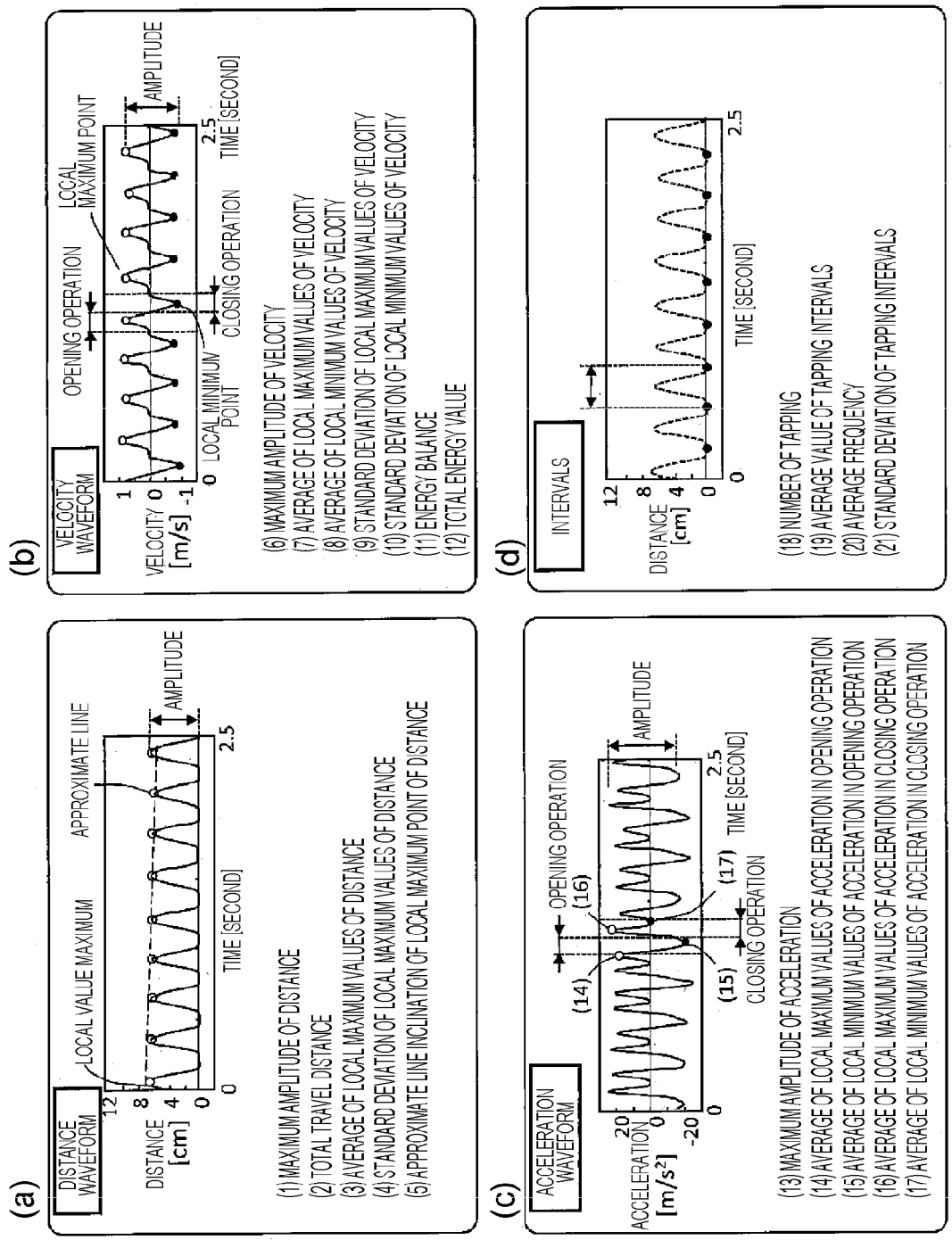
FIGS. 7(a) to 7(d) are diagrams illustrating relationships between various waveform data of the finger-tapping movement and characteristic amounts calculated based from them.

Based on these waveforms, 21 characteristic amounts illustrated in FIG. 7 (7(*a*)-7(*d*)) are calculated. From the distance waveforms of FIG. 7(*a*), following five characteristic amounts are calculated. A maximum amplitude of distance (1) is a difference between a maximum value and a minimum value of the distance waveform. A total travel distance (2) is a sum of absolute values of distance change amounts within a total measurement time. Then, an average of local maximum values of distance (3) is an average value of a local maximum values of finger-tapping movements (illustrated in FIG. 7), and a standard deviation of local maximum values of distance (4) is a standard deviation of local maximum values of every finger-tapping movement. An approximate straight line inclination of distance local maximum point (5) is an inclination of an approximate straight line of a local maximum point (illustrated in FIG. 7) and is supposed to mainly express a change of the amplitude caused by tiredness during the measurement time.

Similarly, from velocity waveforms (FIG. 7(*b*)) obtained by differentiating the distance waveforms, following seven characteristic amounts are calculated. A velocity maximum amplitude (6) is a difference between a maximum value and a minimum value of velocity waveforms. An average of local maximum values of velocity (7) is an average value of local maximum values of every finger-tapping movement, and an average of local minimum values of velocity (8) is an average value of local minimum values of every finger-tapping movement. Similarly, a standard deviation of local maximum values of velocity (9) is a standard deviation of local maximum values of every finger-tapping movement, and a standard deviation of local minimum values of velocity (10) is calculated as a standard deviation of local minimum values of every finger-tapping movement. Here, the local maximum value of velocity is a maximum value in an opening operation (from a condition that two fingers are closed to a condition that the two fingers are fully opened), and the local minimum value of velocity is a minimum value in a closing operation (from a condition that two fingers are opened and to a condition that the two fingers are closed). Further, an energy balance (11) is a ratio of a square of velocity during the opening operation and a square of velocity during the closing operation. A total energy value (12) is a square of velocity during the entire measurement time.

Further, regarding the acceleration waveforms of FIG. 7(*c*) obtained by differentiating the velocity waveform, following five characteristic amounts are calculated. The maximum amplitude of acceleration (13) is a difference between a maximum value and a minimum value of the acceleration waveforms. Further, focusing on four types of extreme values found in one cycle of tapping, an average of local maximum values of velocity in an opening operation (14), an average of local maximum values of velocity in an opening operation (15), an average of local maximum values velocity in a closing operation (16), and an average of local minimum value of velocity in a closing operation (17) are calculated (all values are illustrated in FIG. 7(*c*)). These characteristic amounts respectively correspond to operating forces at a timing that the two fingers start to open, a timing that the fingers are opened, a timing that the fingers are closed, and a timing that the fingers start to close.

In final, from data of tapping intervals of FIG. 7(*d*), four characteristic amounts are calculated. A number of tapping (18) is a number of finger-tapping movements during the entire measurement time. A tapping interval average value (19) is an average value of tapping intervals (illustrated in FIG. 7(*d*)) which are intervals from a local minimum point to a next local minimum point of the distance waveforms. An advantage frequency (20) is a frequency that a spectrum becomes maximum when the distance waveform is converted by Fourier transform. A standard deviation of tapping intervals (21) represents a standard deviation of the tapping intervals.

[Evaluation Value]

Next, the evaluation value will be described. The evaluation value is a numerical value which is previously given to a sample. It may be a numerical value obtained from scoring by a person or may be a numerical value obtained from an experimental result. It may be any index if it is a numerical value obtained by evaluating a sample based on a predetermined standard.

According to the present embodiment, as an evaluation value, the UPDRS ft which is an evaluation scale scored by a doctor is used. The UPDRS ft is an item of UPDRS which is a PD evaluation scale and an integer value of five levels of 0≤UPDRS ft≤4. In case that UPDRS ft=0, the finger-tapping movement is understood to be normal and, as it becomes closer that UPDRS ft=4, increases severity is indicated.

In the medical field, in addition to the UPDRS used in the present embodiment, there are various evaluation scales such as Yahr's severity classification used for PD diagnosis, a UHDRS (Unified Huntington's Disease Rating Scale) used for Huntington's disease diagnosis, a SARA (Scale for the Assessment and Rating of Ataxia) used for an ataxi adiagnosis, a MMSE (Mini-Mental State Examination) used for a dementia diagnosis, and the like.

Sample Group Used in the Present Embodiment

As a sample group to which the present invention is applied, finger-tapping movements were tested with an unimpaired group of 196 individuals (males and females of age 50 to 70) and a PD patient group of 28 individuals (males and females of age 60 to 70). As described above, since it is difficult to obtain data of a patient group, the number of individuals in the PD patient group is a small number of 28. In the test, an instruction "as wider as possible and as fast as possible" was given and finger-tapping movements of a right hand was tested for 30 seconds. Based on obtained waveforms, the above 21 characteristic amounts were calculated. Further, a UPDRS ft score that a doctor visually observed and scored the finger-tapping movement was recorded as an evaluation value.

Characteristic amounts and evaluation values obtained in the above sample group are described in the diagram of FIGS. 8(a) and 8(b). As illustrated in FIG. 8(a), in the unimpaired group, each unimpaired individual has number of characteristic amounts and an evaluation value is not given. In the PD patient group, each PD patient is given with "p" number of characteristic amounts and an evaluation value. The sample groups in FIG. 8(a) are input to the discrimination/regression process 1 as the sample group 2 of FIG. 2, and characteristic amounts of a new sample of FIG. 8(b) are input to the estimating equation application unit 25 of FIG. 2 as the new sample 3 of FIG. 2 so that the estimated evaluation value 5 is calculated.

<<Definition of Estimating Equation>>

Hereinafter, a configuration and a concrete application method of the present invention will be explained.

According to the present embodiment, the estimating equation is an equation in which a characteristic amount is linearly-combined as Equation 1.

[Mathematical Formula 1]

$$y_e(x) = w_0 + \sum_{p=1}^{P} w_p x_p \quad \text{(Mathematical Formula 1)}$$

In this equation, $x_p$ is characteristic amounts (n=0 to P, P=the number of characteristic amounts) obtained from finger-tapping movement data, $w_p$ is weight corresponding to each characteristic amount, and $w_0$ is a constant term. The characteristic amount $x_p$ is a characteristic amount after normalizing to cancel a difference in a range among the characteristic amounts. When the characteristic amount before normalization is expressed as $x_{rp}$, $x_p$ can be calculated by $x_p = (x_{rp} - m_p)/\sigma_p$ using an average value $m_p$ and a standard deviation $\sigma_p$ of $x_{rp}$ of the unimpaired group. Here, the value of the original characteristic amount may be used without the normalization in this manner.

The method for creating a new index by linearly combining a plurality of characteristic amounts in this manner is used in many conventional processes such as a discrimination analysis, a multiple regression analysis, and the like. In the present invention, in addition to the estimating equation by linear combination, other formats may be employed if it is an equation in which a plurality of characteristic amounts are input and a single numerical value is calculated. For example, an estimating equation using a basis function $\varphi(x_p)$ of one of (Equation 2a), (Equation 2b) or (Equation 2c) may be applied as substitute for $x_p$ in the right side of (Equation 1).

[Mathematical Formula 2a]

$$\phi(x_p) = \sum_{q=1}^{Q} d_p^q x_p^q \quad \text{(Mathematical Formula 2a)}$$

[Mathematical Formula 2b]

$$\phi(x_p) = \exp\left\{-\frac{(x_p - \mu_p)^2}{2\sigma_p^2}\right\} \quad \text{(Mathematical Formula 2b)}$$

[Mathematical Formula 2c]

$$\phi(x_p) = \frac{1}{1 + \exp\left\{-\frac{x_p - \mu_p}{\sigma_p}\right\}} \quad \text{(Mathematical Formula 2c)}$$

(Equation 2a) expresses the basis function $\varphi(x_p)$ of linear combination as a polynomial equation. Further, (Equation 2b) expresses the basis function as a Gaussian distribution, and (Equation 2c) expresses the basis function as a logistic sigmoid function. Here, since a usage of a kernel method in an optimization of a later described combination evaluation function sometimes makes the calculation easier, the estimating equation may be defined using the kernel method.

Here, in the present embodiment, a single estimating equation is enough since the evaluation value is one type; however, more than one estimating equation need to be defined when a plurality of evaluation values are used.

<<Conversion of Evaluation Value>>

The evaluation value conversion unit 10 (FIG. 3) will be explained. The evaluation value conversion unit 10 includes the evaluation value substitution table creation unit 11, the evaluation value substitution unit 12, and the sample assignment unit 13. In the present embodiment, since the UPDRS ft is not evaluated for the unimpaired group, the evaluation value is absent. Thus, based on following interpretation, the evaluation value is converted into a numerical value range.

The UPDRS ft is expressed as integer values from 0 to 4 and 0 is defined as unimpaired and the number closer to 4 is defined as severer. Considering based on these definitions, when a finger-tapping movement of an unimpaired person is evaluated by the UPDRS ft, it is presumed to be equal to or lower than 0. In other words, as setting UPDRS ft=0 as a border between a PD patient and an unimpaired group, the range of UPDRS ft≤0 is considered to be in the unimpaired group, and the range of UPDRS ft>0 is considered to be in the PD patient group. As described above, according to the present embodiment, evaluation values which are absent in the unimpaired group are converted into a numerical value range which is UPDRS ft≤0.

Here, according to the present embodiment, the loss of the evaluation value is made associated with a numerical value range restricted by a single inequality equation; however, it may be made associated with other numerical values or numerical value distributions. For example, it may be made associated with a numerical value range, which is restricted by two inequality equations using upper and lower restrictions, a function such as a normal distribution, or the like.

Further, in the present embodiment, the absence of the evaluation value is converted; however, an evaluation value without absence may be converted into a numerical value distribution. For example, regarding the PD patient group to which a UPDRS ft score is given in advance, it may be considered a case to convert (evaluation value UPDRS ft=0) into (−0.5≤UPDRS ft<0.5), (evaluation value UPDRS ft=1) into (0.5≤UPDRS ft<1.5), (evaluation value UPDRS ft=2) into (1.5≤UPDRS ft<2.5), (evaluation value UPDRS ft=3) into (2.5≤UPDRS ft<3.5), and (evaluation value UPDRS ft=4) into (3.5≤UPDRS ft<4.5). FIGS. 9(a) and 9(b) are conceptual diagrams illustrating a conversion of the evaluation values into numerical value distributions. In other words, FIG. 9(a) illustrates a correspondence relationship between unconverted evaluation values and estimated evaluation values, and FIG. 9(b) illustrates a correspondence relationship between the evaluation values which are already converted into numerical value distributions and the estimated evaluation values.

When the evaluation value given as a numerical value is substituted with a numerical value distribution in this manner, there is an advantage that discreteness of the evaluation values can be reduced. The reduction of the discreteness will be concretely described. Even when some subjects have the same evaluation value, some of them may be subjects with a mild symptom and some may be subjects with a sever symptom. However, since the doctor evaluates by a visual observation, it is difficult to grade in a more detailed evaluation scale than the current five levels. Here, this problem is solved by substituting the evaluation value with a numerical value distribution. Concretely, as illustrated in FIG. 8(b), when (UPDRS ft=1) is substituted with (0.5≤UPDRS ft<1.5), among the subjects evaluated as (UPDRS ft=1), a subject with a milder symptom may be given an evaluation value closer to (UPDRS ft=0.5) and a subject with a severer symptom may be given an evaluation value closer to (UPDRS ft=1.5), so that the evaluation scale can fits the reality. When the discreteness is reduced in this manner, regression effect (a phenomenon that an estimated value becomes closer to an average value when an error within a sample group is large) can be reduced.

Considering the present embodiment in the same manner, while the unimpaired group is evaluated all (UPDRS ft=0) if a doctor evaluates, it may be considered that the discreteness was reduced by substituting with a numerical value distribution of (UPDRS ft≤0).

Here, according to the present embodiment, a numerical value, a numerical value distribution, or a numerical value range is associated with a single sample; however, two or more of the numerical value, numerical value distribution and numerical value range may be associated with a single sample. By doubly associating in this manner, when the same sample is used in both of the regression and discrimination, the evaluation value can be calculated as a numerical value range in the discrimination evaluation function and the evaluation value can be calculated as a numerical value in the regression evaluation function.

<<Calculation of Combination Evaluation Function>>

A method for calculating a combination evaluation function 20(E) will be explained. For the explanation, a discrimination evaluation function 17($E_d$) for evaluating the discrimination accuracy between the unimpaired group and the patient group and a regression evaluation function 16($E_r$) for evaluating the accuracy of a severity quantification of the patient group, which are required in the process of E calculation, will be defined. Hereinafter, both calculation methods will be explained in order of the regression evaluation function $E_r$ and the discrimination evaluation function $E_d$.

[Calculation of Regression Evaluation Function]

The regression evaluation function calculation unit 14 (FIG. 1, FIG. 2, or FIG. 3) will be explained. The regression evaluation function 16($E_r$) is an evaluation function that expresses a severity quantification of the patient group. Here, $E_r$ is made to be the same as an error function defined in the multiple regression analysis. In other words, as expressed in (Equation 3a), a summation of square of an error between the evaluation scale $y_{ri}$ and the estimated evaluation value $y_{ei}$ is calculated for all samples of the patient group (i=1 to $N_r$, $N_r$ is the number of samples used in regression).

[Mathematical Formula 3a]

$$E_r = \sum_{i=1}^{N_r} (y_{ri} - y_{ei})^2 \text{ where}$$

(Mathematical Formula 3a)

Figure 10:
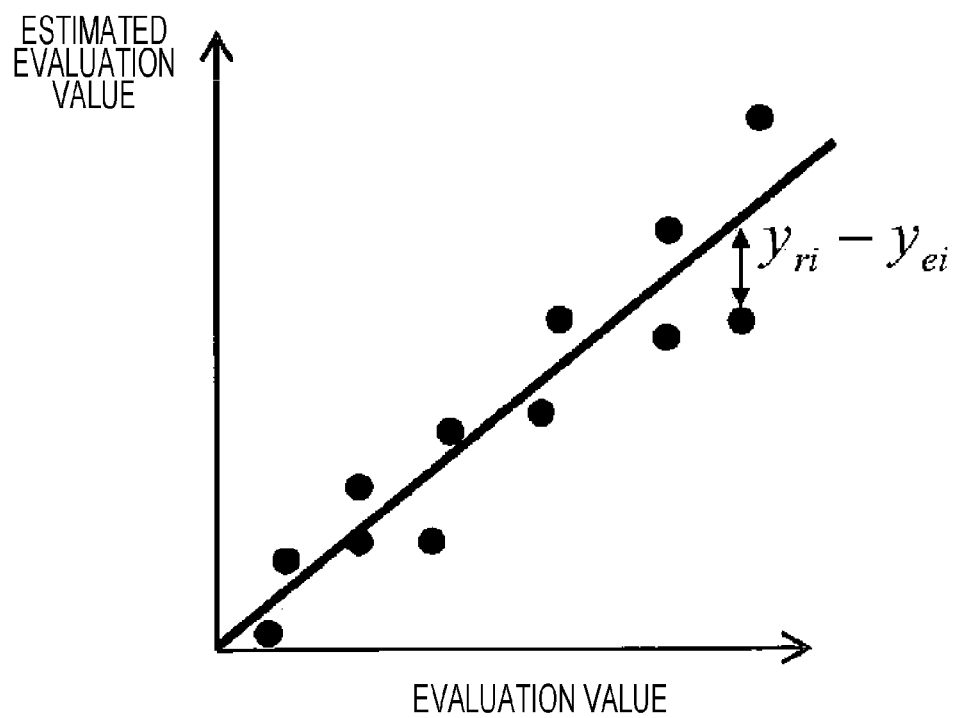
FIG. 10 is a conceptual diagram explaining a regression evaluation function using an error sum of squares.

$\begin{cases} N_r\text{: the number of samples used in regression} \\ y_{ri}\text{: previously given evaluation value } (i = 1 \text{ to } N_r) \\ y_{ei}\text{: estimated evaluation value } (i = 1 \text{ to } N_r) \end{cases}$ FIG. 10 illustrates a concept of calculation of regression evaluation function using the error sum of squares. As understood from the definition of (Equation 3a), $E_r$ represents a degree of diremption of the estimated evaluation value $y_e$ from the evaluation scale $y_r$. In other words, as $E_r$ becomes smaller, the accuracy of the estimated evaluation value $y_e$ increase. Thus, in order to improve the accuracy of severity quantification of the patient group, $E_r$ needs to be minimized.

Other equation as a substitute for the equation shown as (Equation 3a) may be used, as long as $E_r$ is an evaluation function that expresses the accuracy of the severity quantification of the patient group. For example, in order to avoid over-fitting, a case may be considered that an evaluation function like (Equation 3b) is used by adding a regularization term (square sum of factor $w_n$ of the estimating equation, or the like).

[Mathematical Formula 3b]

$$E_r = \sum_{i=1}^{N_r} (y_r - y_e)^2 + \lambda \|w\|^2 \text{ where} \quad \text{(Mathematical Formula 3b)}$$

$w = (w_0, w_1, \ldots w_p)$
$\lambda \geq 0$: constant of regularization term

As another example of a definition of $E_r$, an evaluation function such as an equation of (Equation 3c) may be considered.

[Mathematical Formula 3c]

$$E_r = \sum_{i=1}^{N_r} \xi(y_{ri} - y_{ei}) + \frac{\lambda}{2}\|w\|^2 \text{ where} \quad \text{(Mathematical Formula 3c)}$$

$$\begin{cases} N_r: \text{ the number of samples used in regression} \\ y_{ri}: \text{ previously given evaluation value } (i = 1 \text{ to } N_r) \\ y_{ei}: \text{ estimated evaluation value } (i = 1 \text{ to } N_r) \\ w = (w_0, w_1, \ldots \dot{w}_P) \\ \xi(z) = \begin{cases} 0 & \text{if } |z| < \varepsilon \\ |z| - \varepsilon & \text{otherwise} \end{cases} \end{cases}$$

Figure 11:
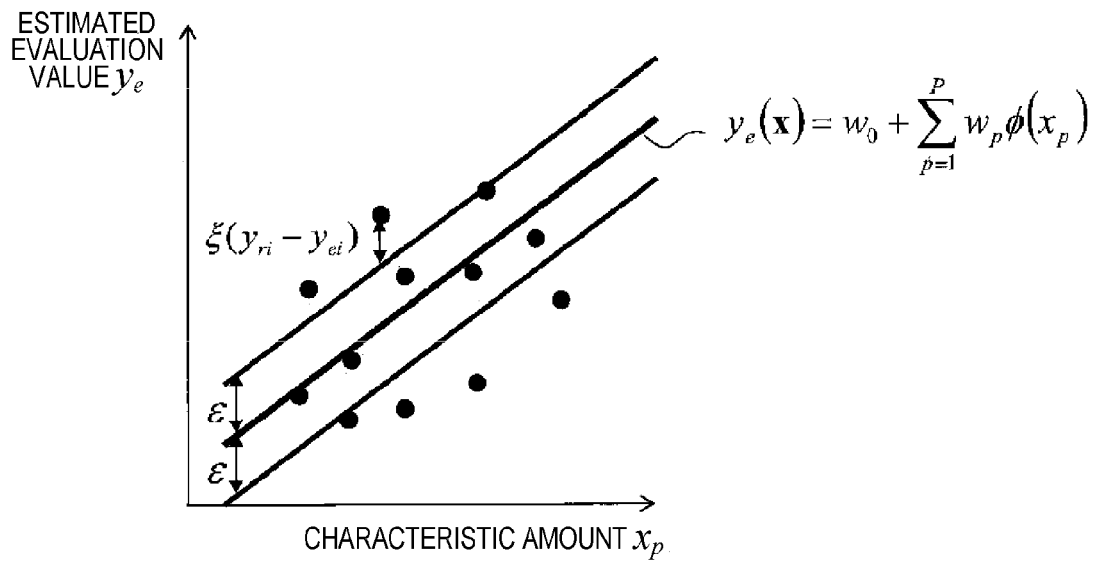
FIG. 11 is a conceptual diagram explaining a regression evaluation function using an SVM.

This evaluation function is an evaluation function related to a margin maximization used in an SVM regression (Support Vector Machine Regression). In other words, as illustrated in FIG. 11, two hyperplanes being separated from estimating equation equal to or more than E are presumed and a penalty in proportion to a distance from the hyperplanes is given only to a sample distributed outside the hyperplanes. Here, regarding $E_r$, when the number of samples having the same evaluation value differs, it is preferable to regularize each group with the number of samples. This prevents that the range of $E_r$ changes according to the number of input samples. There is an advantage that a later described priority constant is not easily affected by the number of samples when the regularization is executed. Further, when there are a plurality of evaluation values to be processed in regression and a plurality of estimating equations are defined accordingly, $E_{rk}$ (k represents each evaluation value) is respectively defined and each $E_{rk}$ is weighted and added to calculate $E_r$. Here, as the method for combining $E_{rk}$, other methods may be employed.

[Calculation of Discrimination Evaluation Function]

Next, the discrimination evaluation function calculation unit 15 (FIG. 1, FIG. 2 or FIG. 3) will be explained. When only $E_r$ is minimized as described above, the accuracy of the discrimination for the patient group and the unimpaired group may not be increased at the same time even when the accuracy of the severity quantification improves. Thus, the discrimination evaluation function 17($E_d$) for evaluating the accuracy of the discrimination for the unimpaired group and patient group, which is expressed as (Equation 4), is introduced.

[Mathematical Formula 4]

$$E_d = \sum_{i, y_{ei}>0}^{N_d} (y_{ei} - 0)^2 \text{ where} \quad \text{(Mathematical Formula 4)}$$

$N_r$: the number of samples used in regression
$y_{ei}$: estimated evaluation value ($i = 1$ to $N_d$)

This equation expresses that a summation of square of an error from 0 is calculated for only data of (estimated evaluation value $y_{ei}>0$) in the unimpaired group.

When the regression evaluation function $E_r$ is minimized, in the patient group, since the estimated evaluation value $y_e$ becomes close to the evaluation scale $y_r$ of the patient group, it basically becomes ($y_e>0$). Based on the above, when ($y_e \leq 0$) is satisfied in the unimpaired group in contrast, it enables to discriminate the patient group and the unimpaired group by using $y_e$. According to this consideration, (Equation 4) selects only data in which ($y_e \leq 0$) is not satisfied (that is, data of ($y_e>0$)) in the unimpaired group and gives a greater penalty to those being further from ($y_e=0$) (FIG. 11). Thus, when the discrimination evaluation function $E_d$ is minimized, since many pieces of data in the unimpaired group satisfy ($y_e \leq 0$), it becomes easier to discriminate the unimpaired group from the patient group which is ($y_e>0$). In this manner, the discrimination evaluation function calculation unit 15 calculates $E_d$ so as to satisfied the limitation, targeting a sample in which its evaluation value is substituted with a numerical value range or a numerical value distribution by the evaluation value conversion unit 10.

In addition to the above, other evaluation functions may be defined if it is an evaluation function expressing the accuracy of discrimination between two or more groups. For example, as expressed by (Equation 5), an evaluation function which is used in Fisher's linear discrimination analysis may be employed.

[Mathematical Formula 5]

$$E_d = \frac{S_B}{S_W} = \frac{(m_2 - m_1)^2}{s_1^2 + s_2^2} \text{ where} \quad \text{(Mathematical Formula 5)}$$

$$\begin{cases} m_k = \frac{1}{n_k} \sum_{y_e \in C_k} y_e \\ s_k = \sqrt{\sum_{y_e \in C_k} (y_e - m_k)^2} \\ C_k: \text{class } (k = 1, 2) \end{cases}$$

Figure 12:
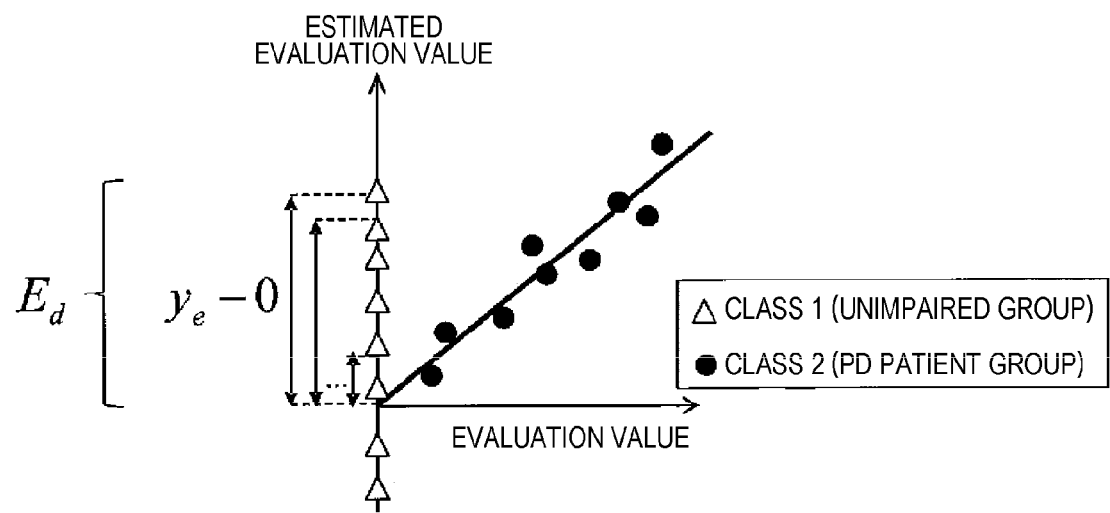
FIG. 12 is a conceptual diagram explaining a discrimination evaluation function using an error sum of squares.
Figure 13:
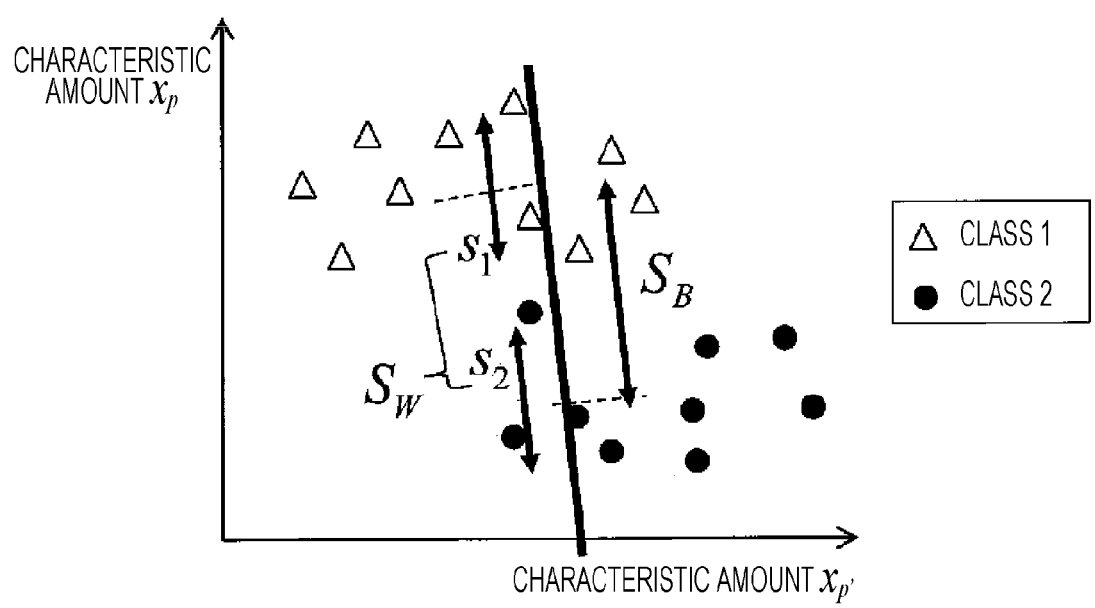
FIG. 13 is a conceptual diagram explaining an discrimination evaluation function using a Fisher's linear discrimination analysis.

This evaluation function means a ratio of a between-class variance $S_B$ in a within-class variance $S_W$. Here, the between-class variance $S_B$ expresses an average value of a plurality of groups and the within-class variance $S_W$ expresses a variability within each group (see FIG. 12). With a larger between-class variance $S_B$ and a smaller within-class variance $S_W$, the two classes can be discriminated with a higher accuracy. Thus, when the evaluation function is maximized, an estimating equation with a high discrimination performance can be obtained.

In addition to the above, an evaluation function like (Equation 6) may be employed.

[Mathematical Formula 6]

$$E_d = \sum_{i=1}^{N_d} \xi_i + \frac{\lambda}{2}\|w\|^2 \text{ where}$$

(Mathematical Formula 6)

$$\begin{cases} w = (w_0, w_1, \ldots w_P) \\ N_d: \text{the number of samples used in discrimination} \\ \xi_i \geq 0 \\ t_i y_{ei} \geq 1 - \xi_i \\ t_i = \begin{cases} 1 & (\text{class 1}) \\ -1 & (\text{class 2}) \end{cases} \end{cases}$$

Figure 14:
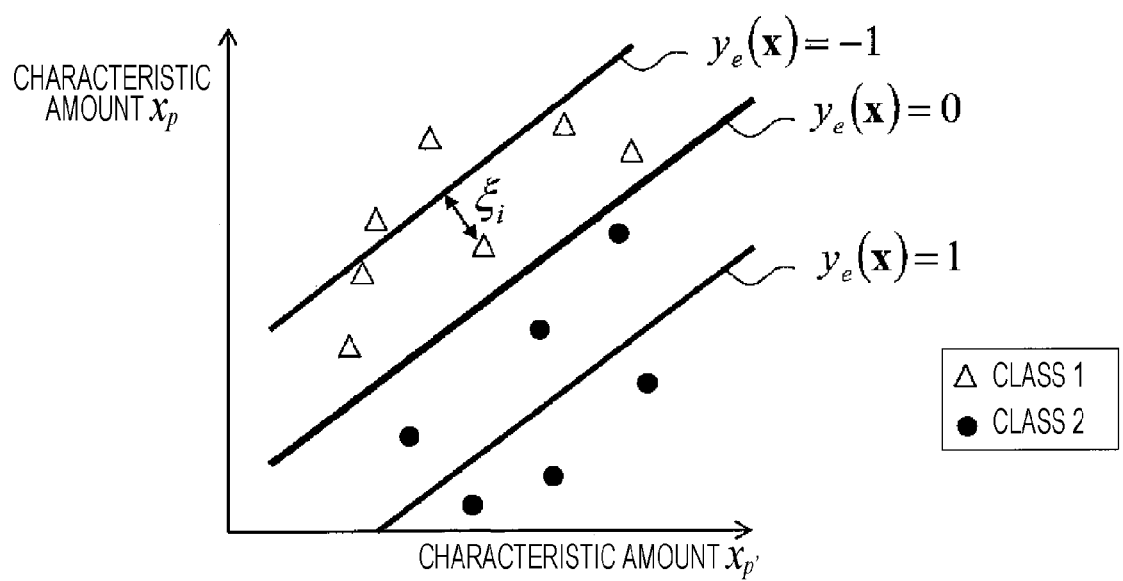
FIG. 14 is a conceptual diagram explaining a discrimination evaluation function using SVM.

This evaluation function is an evaluation function related to a margin maximization used in a discrimination by the SVM. When the evaluation function is maximized, as illustrated in FIG. 14, with a hyperplane ($y_e(x)=0$) as a border, two classes of class 1 and class 2 can be discriminated (class 1: $t_i=1$, class 2: $t_i=-1$). In (Equation 6), in order to realize a flexible discrimination as accepting an error discrimination, two hyperplanes ($y_e(x)=1$) and ($y_e(x)=-1$) being separated from the border at a certain distance are presumed, a sample distributed outside the hyperplanes is considered as an error discrimination, and a penalty in proportion to a distance $\xi_i$ from the hyperplanes is given to the sample. Here, it is preferable that $E_d$ is regularized with the number of samples. This is to prevent that the range of $E_d$ changes according to the number of input samples. There is an advantage that, when a regularization is executed, a later described priority constant c is not easily affected by the number of samples. Further, when discriminating three or more groups, the above calculation is executed for two groups respectively to calculate $E_{dk}$ (k is a combination of two groups) and then each $E_{dk}$ is combined to calculate $E_d$.

[Combining Regression Evaluation Function and Discrimination Evaluation Function]

The combination evaluation function calculation unit 18 (FIG. 1, FIG. 2 or FIG. 3) will be explained. As described above, the regression evaluation function 16 ($E_r$) that expresses the accuracy of the discrimination between the unimpaired group and the patient group, and the discrimination evaluation function 17 ($E_d$) that expresses the accuracy of the severity quantification of the patient group are defined, and it has been described that the functions needs to be minimized. However, in general, since $w_n$ that optimizes $E_d$ and $w_n$ that optimizes $E_r$ cannot be equal, $E_d$ and $E_r$ cannot be optimized at the same time. Thus, $c_1$ and $c_2$ are introduced as priority constants 1901 to adjust the priority of those functions and a combination evaluation function E like (Equation 7a) is defined so that E is optimized.

[Mathematical Formula 7a]

$$E = c_1 E_d + c_2 E_r$$
where $c_1$, $c_2$: priority constant (Mathematical Formula 7a)

Here, $c_2$ is made to be a large value to emphasize the accuracy of the severity quantification and, on the other hand, $c_1$ is made to be a large value to emphasize the accuracy of the discrimination between the patient group and the unimpaired group. Further, ultimately, it may be set as ($c_2=0$) to eliminate the effect of the severity quantification and it may be set as ($c_1=0$) to eliminate the effect of the discrimination. These cases are the same as the case in which the discrimination process or the regression process is applied respectively.

Here, in the present embodiment, two constants of $c_1$ and $c_2$ are set as the priority constants 1901, the number of the priority constants 1901 is not limited to two. For example, as an equation illustrated as (Equation 7b), it may be considered a case that E is defined by calculating a product of $E_d$ and $E_r$ using c.

[Mathematical Formula 7b]

$$E = E_d{}^c E_r{}^{(1-c)}$$
where $c_1$, $c_2$: priority constant (Mathematical Formula 7b)

Further, E may be calculated by using only $E_d$ and $E_r$ without setting the priority constant 1901. In this case, a later described process for adjusting the priority of the regression and discrimination is not necessary.

[Priority Adjustment of Regression and Discrimination]

The discrimination/regression priority adjusting unit 19 (FIG. 2) will be explained. In the present embodiment, the priority constants 1901 are set as ($c_1=0.2$) and ($c_2=1.0$). However, $c_1$ and $c_2$ may be a searched numerical value which maximizes discrimination performance or regression performance without using a predetermined numerical value. For example, regarding the discrimination accuracy, based on an AUC (Area Under the ROC Curve) as a standard, it may be considered a method for searching c so that the AUC becomes maximized using a golden section method. In addition, a summation of squared error of an estimated evaluation value estimated using the estimating equation obtained by optimizing E and an evaluation value given to the sample group may be minimized. These evaluations are preferably executed by using a LOO method (Leave one out method), a cross validation method and the like.

Further, in addition to the golden sectional method, the method for optimizing the index expressing the accuracy of the estimating equation 24 may be any method such as a Newton's method, a quasi-Newton's method, a simplex method, a neural network, or the like as long as the method can optimize the function.

<<Optimization of Combination Evaluation Function>>

The combination evaluation function optimization unit 21 (FIG. 1, FIG. 2 or FIG. 3) will be explained. The above described combination evaluation function 20(E) is minimized by the quasi-Newton's method. The quasi-Newton's method is a method to reduce a calculation amount by approximating an inverse matrix of a Hessian matrix used in the Newton's method by a BFGS formula. As a step size used in the quasi-Newton's method, the golden section method which is a type of a primary search method is used. The method for sequentially minimizing a function, such as the quasi-Newton's method, is used in this manner as a method for minimizing the combination evaluation function E in this manner because the combination evaluation function cannot be analytically optimized in general. When the combination evaluation function E is defined to be analytically optimized, a sequential solution method is not necessary to be used.

Here, according to the present embodiment, the optimistic estimating equation 24 is obtained by minimizing the combination evaluation function E; however, when an evaluation function, which realizes regression or discrimination by maximizing in a manner of the equation of (Equation 3c) or the equation of (Equation 6), is used, the combination evaluation function E needs to be maximized. Further, according to the present embodiment, the quasi-Newton's method is used to optimize E; however, other optimization methods may be employed. For example, there are a steepest descent method, a Newton's method, a simplex method, a neural network, and the like.

In particular, when the equation of (Equation 3c) is used for a regression discrimination function 16($E_r$) and the equation of (Equation 6) are used for a discrimination evaluation function 17($E_d$), a quadratic programming problem solution method generally used in SVM may be used. Concretely, a case will be considered that $E_1$ is defined as the equation of (Equation 6), $E_r$ is defined as the equation of (Equation 3a), and E combined of $E_d$ and $E_r$ is defined as the equation of (Equation 7a). In this case, $E_d$ can be converted to $E'_d$ shown in an equation of (Equation 8a) by being converted to a dual representation after converted to a Lagrangian function. Similarly, $E_r$ can be converted into $E'_r$ shown in an equation of (Equation 8b) by being converted to a dual representation after converted to a Lagrangian function'.

[Mathematical Formula 8a]

(Mathematical Formula 8a)

$$E'_d(a) = \sum_{i=1}^{N_d} a_i - \frac{1}{2} \sum_{i=1}^{N_d} \sum_{j=1}^{N_d} a_i a_j t_i t_j k(x_i, x_j)$$

where $$\begin{cases} a_i: \text{Lagrange multiplier} \\ k(x_i, x_j): \text{kernel of } x_i \text{ and } x_j \\ t_i: \text{class (1 or } -1) \\ N_d: \text{the number of samples used in discrimination} \\ 0 \le a_i \le C_d \\ \sum_{i=1}^{N_d} a_i t_i = 0 \end{cases}$$

[Mathematical Formula 8b]

(Mathematical Formula 8b)

$$E'_r(b, \hat{b}) =$$

$$-\frac{1}{2}\sum_{i=1}^{N_r}\sum_{j=1}^{N_r}(b_i - \hat{b}_i)(b_j - \hat{b}_j)k(x_i, x_j) - \varepsilon\sum_{i=1}^{N_r}(b_i + \hat{b}_i) + \sum_{i=1}^{N_r}(b_i - \hat{b}_i)t'_i$$

where $$\begin{cases} b_i, \hat{b}_i : \text{Lagrange multiplier} \\ k(x_i, x_j): \text{kernel of } x_i \text{ and } x_j \\ t'_i: \text{evaluation value} \\ N_r: \text{the number of samples used in discrimination} \\ \varepsilon: \text{error acceptable range} \\ 0 \le b_i \le C_r, 0 \le \hat{b}_i \le C_r \\ \sum_{i=1}^{N_c} (b_i - \hat{b}_i) = 0 \end{cases}$$

Based on these conversions, E can be converted to dual representation E' of an equation shown as (Equation 9).

[Mathematical Formula 9]

(Mathematical Formula 9)

$$E'(a, b, \hat{b}) = c_1\left(\sum_{i=1}^{N_d} a_i - \frac{1}{2}\sum_{i=1}^{N_d}\sum_{j=1}^{N_d} a_i a_j t_i t_j k(x_i, x_j)\right) +$$

$$c_2\left(-\frac{1}{2}\sum_{i=1}^{N_r}\sum_{j=1}^{N_r}(b_i - \hat{b}_i)(b_j - \hat{b}_j)k(x_i, x_j) - \right.$$

$$\left. \varepsilon\sum_{i=1}^{N_r}(b_i + \hat{b}_i) + \sum_{i=1}^{N_r}(b_i - \hat{b}_i)t'_i\right)$$

where $$\begin{cases} a_i, b_i, \hat{b}_i : \text{Lagrange multiplier} \\ k(x_i, x_j): \text{kernel of } x_i \text{ and } x_j \\ t_i: \text{class used in discrimination}(1 \text{ or } -1) \\ t'_i: \text{evaluation value used in regression} \\ N_d: \text{the number of samples used in discrimination} \\ N_r: \text{the number of samples used in regression} \\ \varepsilon: \text{error acceptable range} \\ c_1, c_2: \text{priority constant} \\ 0 \le a_{i'} \le C_d, 0 \le b_i \le C_R, 0 \le \hat{b}_i \le C_R \\ \sum_{i=1}^{N_d} a_i t_{i'} = 0, \sum_{i=1}^{N_r} (b_i - \hat{b}_i) = 0 \end{cases}$$

After that, an optimistic estimating equation can be obtained by maximizing E" with a Sequential Minimal Optimization (SMO). Here, as a substitute for the Sequential Minimal Optimization, other methods such as a chunking, a decomposition method, a protected conjugate gradient or the like can be employed as long as it is a method that can solve the quadratic programming problem. Here, E may be directly optimized by using a steepest descent method or the like without converting E to dual representation E'.

<<Convergence Test of Optimization of Combination Evaluation Function>>

The convergence determination unit 22 (FIG. 2) will be explained. In the present embodiment, optimization of the combination evaluation function 20 is executed only once. However, by giving the optimization result to the evaluation value substitution table creation unit 11 of the evaluation value conversion unit 10 as feedback, optimization may be executed again by recalculating the combination evaluation function. In this case, a convergence test is executed on the result of the re-optimization and, when convergence is not enough, feedback is further given to the evaluation value substitution table creation unit 11. When the convergence is enough, the estimating equation 24 is output.

<<Application of Estimating Equation>>

The estimating equation application unit 25 (FIG. 1, FIG. 2 or FIG. 3) will be explained. As described above, the characteristic amount 301 of the new sample 3 is input to the estimating equation 24 which is obtained by optimizing the combination evaluation function 20(E) and the estimated evaluation value 5 is obtained. This estimated evaluation value 5 is an output of this method. According to the present embodiment, a UPDRS ft score can be estimated from finger-tapping movement data of a new subject even when whether the subject has PD and the severity of PD are unknown.

<<Selection of Important Characteristic Amount>>

The important characteristic amount selection unit 23 (FIG. 2) will be explained. In a process to calculate the estimating equation by optimizing the combination evaluation function, an important characteristic amount 4 can be selected from a plurality of characteristic amounts. The important characteristic amount 4 indicates a characteristic amount which has a significant impact when an evaluation value is estimated. There may be more than one important characteristic amounts 4. According to the present embodiment, using a correlation factor between the estimated evaluation value 5 and the characteristic amount $x_n$ as a standard, the characteristic amount $x_n$ which has the highest correlation factor is determined as the important characteristic amount 4.

As a standard to select the important characteristic amount 4, other indexes may be used. For example, it may be considered that a sum of squared residuals between the estimated evaluation value 5 obtained from the estimating equation 24 which is obtained by optimizing the combination evaluation function 20 and the actual evaluation value is used as a standard. Further, a determination factor or an F-measure may be used as a standard.

The important characteristic amount 4 which is selected in this manner is given to the characteristic amount 201 as feedback and the discrimination/regression process may be re-executed with only the selected important characteristic amount 4. This prevents a multicollinearity caused by too many characteristic amounts and the accuracy of the estimating equation improves.

<<System Operation Procedure>>

In the present invention for calculating the estimating equation 24, calculation may be executed only once in the beginning or calculation may be re-executed every time the sample group is increased or changed. In the former case, the estimated evaluation value 5 can be calculated when the system stores only the calculated estimating equation 24. In the latter case, the system needs to store sample group 2 for every calculations.

<<Evaluation of the Present Invention>>

[Evaluation Procedure of the Present Invention]

An evaluation of the present invention employs a LOO (Leave One Out) method. The LOO method is a method for evaluating by dividing "N" number of pieces of evaluation data into "N−1" pieces of learning data and one piece of testing data (N=the number of pieces of the unimpaired groups+the number of pieces of the patient group). In other words, the evaluation is repeated "N" times as changing the combination so that all pieces evaluation data are used as testing data once. Even if a model is learned with "N" pieces of data without using the LOO method and the accuracy of the model by evaluating the same "N" pieces of data is high, there is a problem that the accuracy may not always high for unknown data. The LOO method can solve the problem by recognizing one of the pieces of evaluation data as unknown data and evaluate the accuracy of the model correctly.

Here, in order to evaluate the accuracy of the estimated evaluation value of the testing data, a new index is introduced. This is because the present invention aims to realize a discrimination and a regression at the same time, and it is inappropriate to compare the accuracy with the conventional method by focusing only one of the discrimination and the regression. Thus, a later described index is proposed.

The accuracy of the estimated evaluation value of testing data is evaluated based on an error e from the evaluation scale by the following method. When testing data is selected from the patient group, it is set as e=(estimated evaluation value $y_e$−evaluation scale $y_r$)$^2$. When testing data is selected from the unimpaired group, it is set as e=$y_e^2$ in case of estimated evaluation value $y_e$>0 and it is set as e=0 in case of $y_e$≤0. This is because, regarding an unimpaired person, the accuracy of the estimated evaluation value is considered to be higher when the evaluation scale becomes closer to 0 that the estimated evaluation value indicates unimpaired in the unimpaired group. This error e is calculated for every piece of the testing data of the LOO method and an average value thereof is used as the accuracy of the estimated evaluation value. With this definition, when e becomes smaller, the accuracy of the estimated evaluation value becomes higher. Here, besides the above index, other indexes may be used to evaluate as long as the index can evaluate a performance of regression and discrimination. Further, the performances of the regression and discrimination may be evaluated separately.

In this study, in addition to the present invention as a method to propose, a conventional method (using a discrimination analysis and a multiple regression analysis in parallel) is also applied, and the accuracy of severity quantifications in both methods are compared by suing the above error e. Here, in addition to the evaluation with the error e, an evaluation of the discrimination accuracy is also executed with a sensitivity (a ratio to discriminate patient group and disorder) and a specificity (a ratio to discriminate the unimpaired group as disorder). Further, in order to observe a data distribution, the evaluation is executed by applying a model leaned from the "N" pieces of data to the same "N" pieces of data and plotting the estimated evaluation value of all pieces of data, without using the LOO method.

[Application Result of the Present Invention]

A result of applying the present invention to finger-tapping movement data of an unimpaired group and a PD patient group will be described. Then, a result of applying the same data to a conventional method (after discriminating the unimpaired group and PD patient group by a discrimination analysis, calculating evaluation values for only the PD patient group by a multiple regression analysis) will be described and compared with the result of the present invention.

<Result of Applying the Present Invention>

Figure 15:
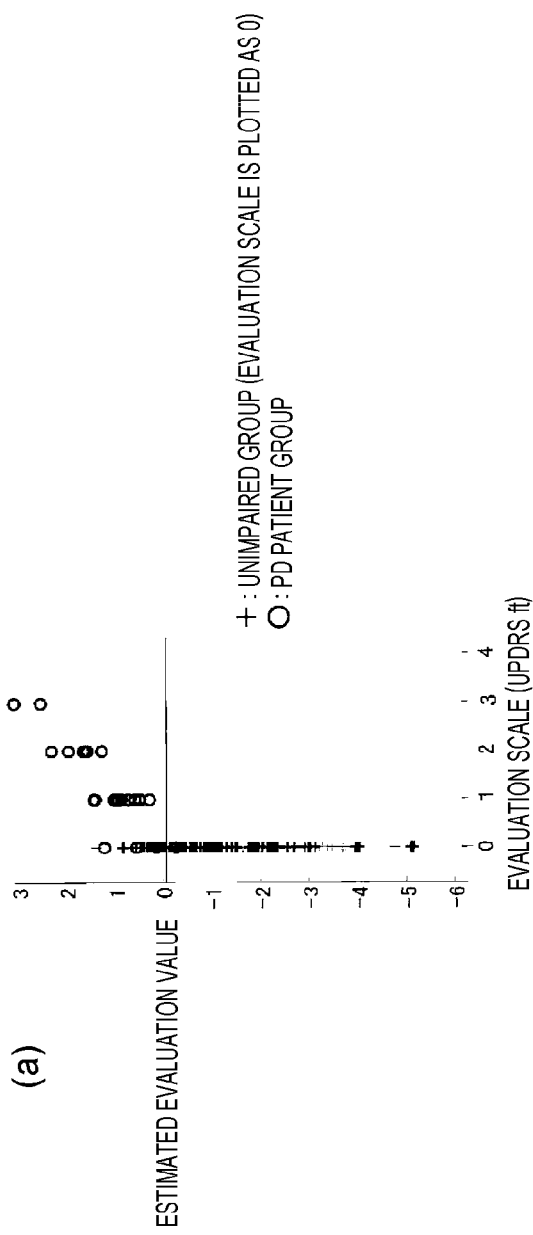
FIGS. 15(a) to 15(c) are graphs illustrating a result of that the present invention is applied to a preferable finger-tapping movement data.

FIG. 15(*a*) is a result of applying the present invention. The horizontal axis represents the UPDRS ft score which is an evaluation scale and the vertical axis represents the estimated evaluation value which is output in the present invention. The sign + represents the unimpaired group and the sign ○ represents the PD patient group. Since the UPDRS ft scores of the unimpaired group are not evaluated, it is plotted as UPDRS ft=0. This result indicates a result of learning a model of "n" pieces of data without using the LOO method and calculating an evaluation value by applying the same data to the model.

Next, a table illustrated in FIG. 15(*b*) is a table showing a discrimination accuracy of the estimated evaluation value by the present invention using the LOO method. It is understood that the sensitivity (a ratio to discriminate patient group and disorder) is 100.0% and the specificity (a ratio to discriminate the unimpaired group as disorder) is 81.6%. A table illustrated in FIG. 15(*c*) is a table showing a result of evaluating the accuracy of the severity quantification by the present invention using the LOO method. It is understood that the unimpaired group is 0.371, the PD patient group is 3.290, and the entire result is 1.648.

<Result of Application of Conventional Method>

Figure 16:
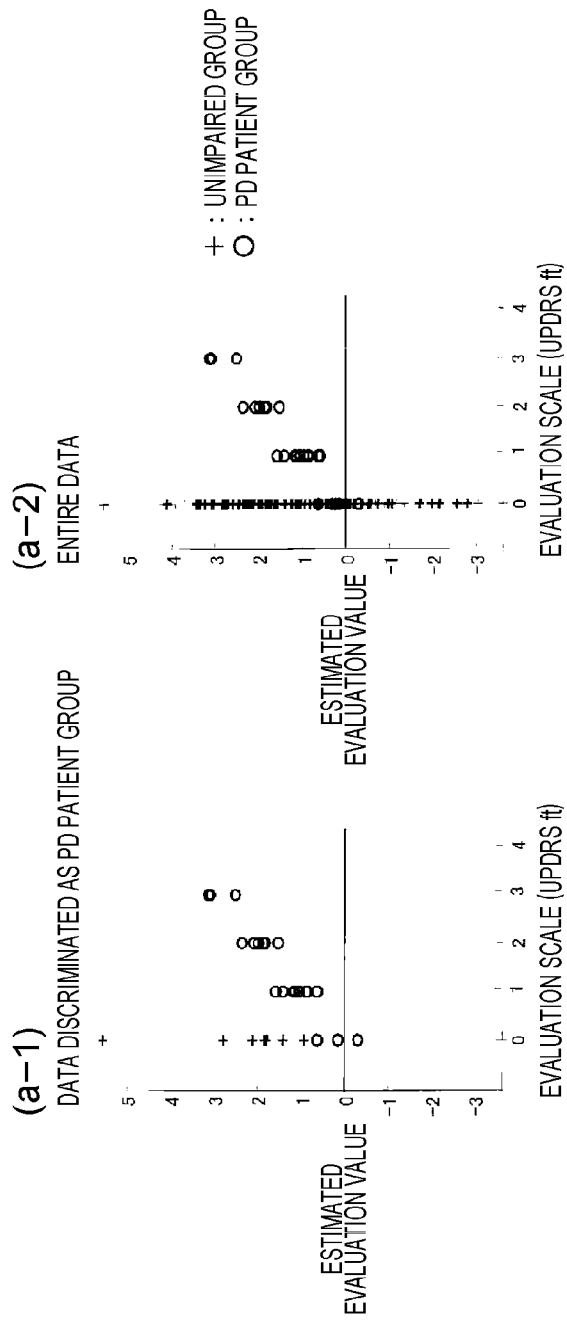
FIGS. 16(a-1) to 16(c) are graphs illustrating a result of applying a conventional method to the finger-tapping movement data.

FIGS. 16(*a*-1) and 16(*a*-2) are results of applying the conventional method (a method for calculating an evaluation value by applying a multiple regression analysis only for the patient group after discriminating the unimpaired group and the patient group by a discrimination analysis) to finger-tapping movement data of the unimpaired group and PD patient group. The horizontal axis represents the UPDRS ft scores as an evaluation scale (an evaluation scale scored by a doctor) and the vertical axis represents the estimated evaluation values output by the multiple regression analysis. The sign + represents the unimpaired group and the sign ○ represents the PD patient group. Since the UPDRS ft score is not evaluated in the unimpaired group, it is plotted as UPDRS ft=0. FIG. 16(a-1) is a chart that plots only data which is discriminated as a patient group in a discrimination analysis. FIG. 16(a-2) is a chart that plots all pieces of data regardless of the discrimination result of discrimination analysis. Here, the results of FIGS. 16(a-1) and 16(a-2) are results of calculation of an evaluation value by learning a model based on "N" number of data without using the LOO method and applying the same data to the model.

The chart shown in FIG. 15(b) is a chart that shows the discrimination accuracy of the conventional method using the LOO method. It is understood that the sensitivity is 89.3% and the specificity is 93.4%. The chart of FIG. 16(c) is results of evaluation of the accuracy of the severity quantification of the present invention using the LOO method. It is understood that the unimpaired group is 6.970, the PD patient group is 5.537, and the entire data is 6.027.
<Comparison of Result of the Present Invention and Result of Conventional Method>

When comparing the discrimination result (the chart of FIG. 15(b)) of the present invention with the discrimination result (the table of FIG. 16(b)) by the discrimination analysis which is a first process of the conventional method, it is understood that the sensitivity is lower by 10.7% and the specificity is higher by 7.8% in the discrimination accuracy. Based on the above, it is understood that the present invention is preferable to discriminate the patient group when the discrimination between the patient group and unimpaired group is ambiguity, comparing with the discrimination analysis. In other words, according to the present invention, it is capable of widely detecting subjects having a possibility of disorder and it may be considered as an algorism preferable to a screening test. Further, comparing the table of FIG. 15(c) with the table of FIG. 16(c), the present invention has the accuracy of the estimated evaluation value for the unimpaired group about 20 times higher than the conventional method and also has the entire accuracy for the unimpaired group and patient group equal to or greater than three times higher of the conventional method.

Next, based on the data distributions (FIG. 15(a) and FIG. 16(a-1)), validity of the estimated evaluation values will be examined. Based on FIG. 16(a-1), it is considered that the estimated evaluation values are invalid since the estimated evaluation value of data of an unimpaired person who is discriminated as the patient group is greater than zero which indicates to be unimpaired and is a value equivalent to the estimated evaluation values of the PD patient group. On the other hand, based on FIG. 15(a), according to the present invention, the estimated evaluation values of the unimpaired group are close to zero and found in the same level with the data of those in the PD patient group with mild symptom. Based on the above, it can be considered that the estimated evaluation value of the present invention are valid.

Further, FIG. 16(a-2) shows a case of calculating an estimated evaluation value for data discriminated as an unimpaired group, based on the result of the multiple regression analysis. In this case, it is understood that there are samples whose estimated evaluation values are calculated greater than zero and equal to or higher than the level of the PD patient group, even it belongs to the unimpaired group. It can be considered that it is invalid that the estimated evaluation value is abnormally high even though it is discriminated as the unimpaired group. The reason is considered that the generalizability is lowered because only the data of a patient group in the multiple regression analysis which is a second process of the conventional method. Concretely, according to the present invention, it is considered that the generalizability can be increased since regression is executed considering the discrimination of the easily-taken unimpaired group and patient group, not only the patient group whose data amount is insufficient.

Summarizing the above, the present invention has a higher accuracy of the severity quantification compared to the conventional method. Further, the conventional method calculates an estimated evaluation value for data discriminated to be a patient group; however, the present invention can calculate an evaluation value regardless of the severity of symptom. With these points, it can be said the present invention is superior to the conventional method.
<Selection Result of Important Characteristic Amount>

In the used 21 characteristic amounts, the characteristic amounts having the highest correlation factor with the estimated evaluation value was the standard deviation (21) of tapping intervals and the correlation factor was 0.4595. It is thus understood that the standard deviation (21) of tapping intervals is the most important characteristic amount when an evaluation value is estimated.

Second Embodiment

A second embodiment will be explained in detail with reference to drawings according to need. In the present embodiment, a discrimination/regression process for a plurality of evaluation values will be described based on the discrimination/regression process explained in the first embodiment. Hereinafter, particularly, a case for estimating severities of two types of disorders will be explained.

Figure 17:
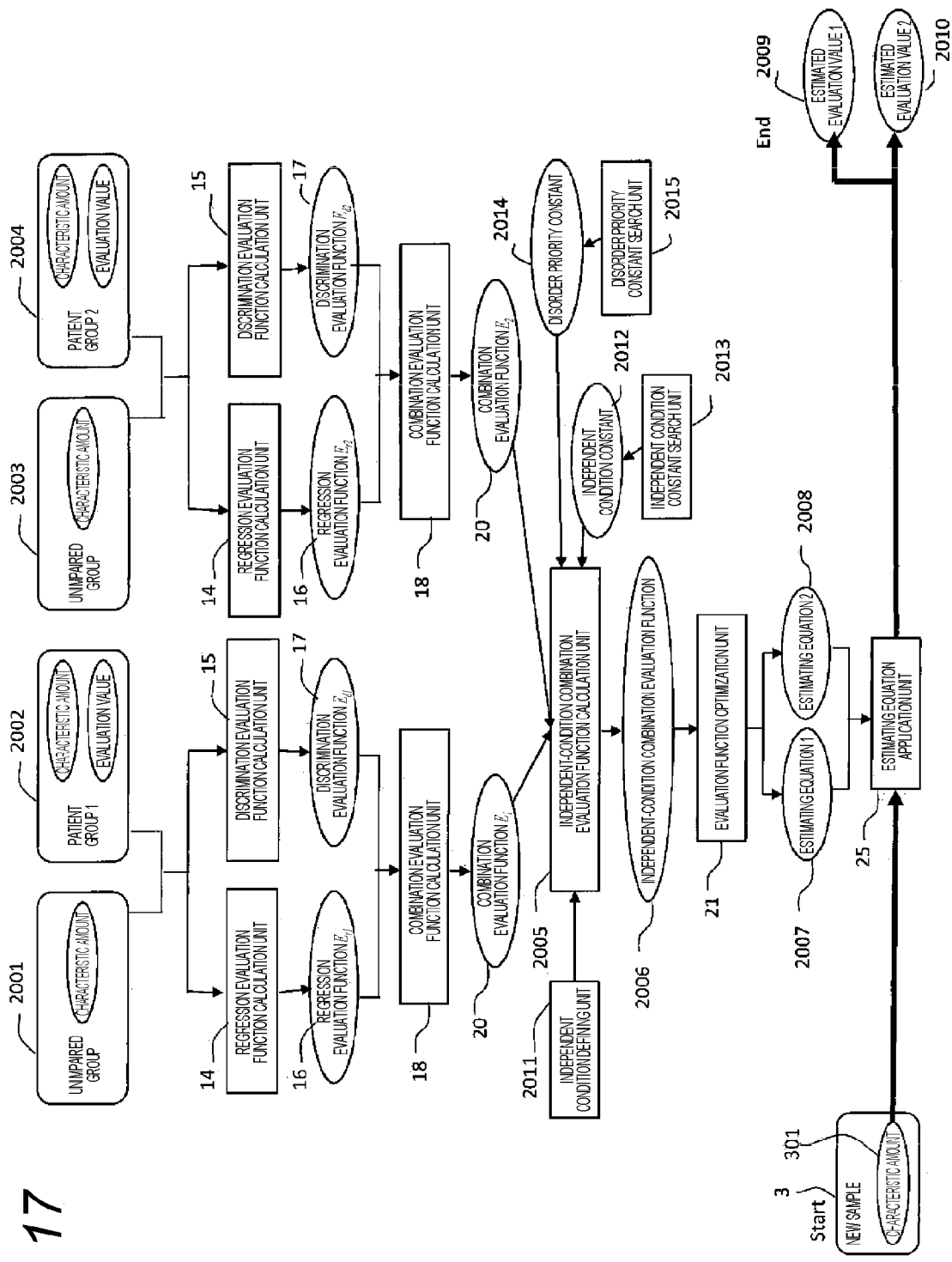
FIG. 17 is a flowchart illustrating a configuration of a discrimination/regression process for a plurality of evaluation values according to a second embodiment of the present invention.

FIG. 17 illustrates a flow of a case for quantifies severities of two type of disorders (patient group 1 and patient group 2). The explanation will be made from the top of the diagram. Firstly, with a method described in the first embodiment, for the patient group 1, a regression evaluation function 16 ($E_r$?), a discrimination evaluation function 17 ($E_{d1}$), and a combination evaluation function 20 ($E_1$) are calculated. Similarly, also for the patient group 2, a regression evaluation function 16 ($E_{r2}$), a discrimination evaluation function 17 ($E_{d2}$), and a combination evaluation function 20 ($E_2$) are calculated. Next, using $E_1$ and $E_2$, a combination evaluation function 2006 (E') with an independent condition is calculated. The part for calculating E' is a different point of the present embodiment from the first embodiment. A method for calculating E' will be described.

The combination evaluation function 2006 (E') with an independent condition is defined by (Equation 10).

[Mathematical Formula 10]

$$E' = (1-c_s)E_1 + c_s E_2 + c_o |T_o| \quad \text{(Mathematical Formula 10)}$$

Here, $E_1$ is a combination evaluation function for a discrimination regression of the unimpaired group and patient group 1, and $E_2$ is a combination evaluation function for a discrimination regression for the unimpaired group and the patient group 2. $c_s$ is a constant (a disorder priority constant 2014) for adjusting the priority of a severity quantification of the disorder 1 and a severity quantification of the disorder 2. $c_s$ is equal to or greater than zero and equal to or less than one. $c_s$ is set as a small value when focusing the accuracy of the severity quantification of the disorder 1 and set as a large value when focusing the accuracy f the severity quantification of the disorder 2. $T_0$ is a variable that expresses a condition that the severity of the patient group 1 and the severity of the patient group 2 become independent (hereinafter, referred to as an independent condition) and will be described in detail. $c_0$ is a constant that defines strength of the independent condition (independent condition constant 2012). $c_0$ is set as a numerical value equal to or greater than zero. The greater value is set as $c_0$, it comes closer to a condition that $y_{e1}$ and $y_{e2}$ are exactly orthogonal.

The above $T_0$ will be explained. $T_0$ is defined by an independent condition defining unit 2011. $T_0$ is a variable that expresses that an estimated severity f the patient group 1 and an estimated severity of the patient group 2 become independent. Here, the condition in which the severity of each patient are independent means that the disorder 1 and disorder 2 are not related with each other and they will never be developed at the same time. In other words, when the severity $y_{e1}$ of the patient is high, the severity $y_{e2}$ of the disorder 2 is low and when the severity $y_{e2}$ of the disorder 2 is high, the severity $y_{e1}$ of the disorder 1 is low.

Figure 18:
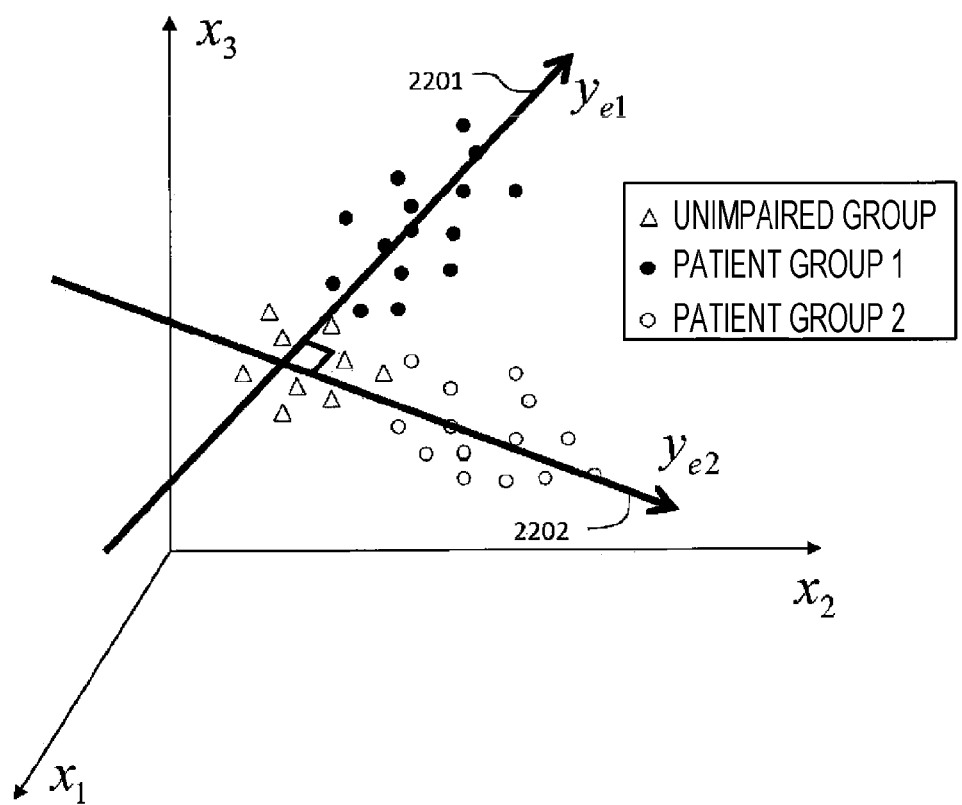
FIG. 18 is a conceptual diagram explaining independence of estimated severity of two types of disorders according to the second embodiment.

The independent condition is a case that an axis of the severity of the patient group 1 and an axis of the severity of the patient group 2 are orthogonal. A pattern diagram of this case is illustrated in FIG. 18. In FIG. 18, a case that the number of characteristic amounts is three is illustrated for the sake of convenience. Thus, the independent condition can be expressed as an inner product of the axis $y_{e1}$ (2201) of the estimated severity of the disorder 1 and the axis $y_{e2}$ (2202) of the estimated severity and the disorder 2, as expressed in (Equation 11).

[Mathematical Formula 11]

$$T_o = \frac{y_{e1} \cdot y_{e2}}{|y_{e1}||y_{e2}|} \quad \text{(Mathematical Formula 11)}$$

Here, for example, $T_0$ is defined as a cosine of $y_{e1}$ and $y_{e2}$ as follows. $T_0$ is in a range of $-1 < T_0 < 1$ according to the angle between $y_{e1}$ and $y_{e2}$. When $y_{e1}$ and $y_{e2}$ face in the same direction, it becomes $T_0=1$, and when $y_{e1}$ and $y_{e2}$ face in different directions, it becomes $T_0=-1$. When $y_{e1}$ and $y_{e2}$ are orthogonal, it becomes $T_0=0$. In other words, only when $y_{e1}$ and $y_{e2}$ are orthogonal, it becomes $|T_0|=0$, and $|T_0|$ becomes larger as the condition becomes further from the orthogonal condition. Thus, it is understood that $|T_0|$ is minimized to make the condition closer to the condition that $y_{e1}$ and $y_{e2}$ are orthogonal. In (Equation 11), in a case that a large value is set as $c_0$, $|T_0|$ becomes a small value when E' is minimized and $y_{e1}$ and $y_{e2}$ come close to a condition of being orthogonal. In contrast, in a case that a small value is set as $c_0$, $|T_0|$ becomes a large value when E' is minimized and $y_{e1}$ and $y_{e2}$ come further from a condition of being orthogonal. Here, as the definition of $T_0$, the above method is not needed to be used, and any method that can express independence of the axes of the a plurality of severity can be used.

Similarly to the first embodiment, E' defined as the above is optimized by the evaluation function optimization unit 21. As a result, an estimating equation 1 (2007) of the severity of the disorder 1 and an estimating equation 2 (2008) of the severity of the disorder 2 can be obtained. With this, the severity (estimated evaluation value 2009) of the disorder 1 and the severity (estimated evaluation value 2010) of the disorder 2 can be obtained. Here, regarding above $c_s$, a numerical value can be set in advance or a numerical value having a high estimated accuracy of the severity may be searched (disorder priority constant search unit 2015). Similarly, regarding above $c_0$, a numerical value may be set in advance or a numerical value having a high estimated accuracy of the severity may be searched (independent condition constant search unit 2013). Further, the disorders described in the present embodiment are two types; however, the idea of the present study may be expanded for three or more types. For example, there may be a method that evaluates independences by combining a pair of axes and obtains $T_0$ by adding the independences.

REFERENCE SIGNS LIST 2 sample group
3 new sample
4 important characteristic amount
5 estimated evaluation value
11 evaluation value substitution table creation unit
12 evaluation value substitution unit
13 sample assignment unit
14 regression evaluation function calculation unit
15 discrimination evaluation function calculation unit
16 regression evaluation function
17 discrimination evaluation function
18 combination evaluation function calculation unit
19 discrimination/regression priority adjusting unit
20 combination evaluation function
21 combination evaluation function optimization unit
22 convergence determination unit
23 important characteristic amount selection unit
24 estimating equation
25 estimating equation application unit
41 state that two fingers are closed
42 state that two fingers are opened
43 magnetic sensor
44 distance between two fingers
51 distance waveform
52 velocity waveform
53 acceleration waveform
101 discrimination process
102 regression process
103 sample group (1)
104 new sample
105 sample group (2)
106 estimated evaluation value
201 characteristic amount of sample group
202 evaluation value of sample group
301 characteristic amount of new sample
1011 discrimination evaluation function calculation unit
1012 discrimination evaluation function
1013 discrimination evaluation function optimization unit
1014 discrimination equation
1015 discrimination equation application unit
1021 regression evaluation function calculation unit
1022 regression evaluation function
1023 regression evaluation function optimization unit
1024 estimating equation
1025 estimating equation application unit
1901 priority constant
1902 priority constant search unit
2001 unimpaired group
2002 patient group 1

2003 unimpaired group
2004 patient group 2
2005 independent-condition combination evaluation function calculation unit
2006 independent-condition combination evaluation function
2007 estimating equation 1
2008 estimating equation 2
2009 estimated evaluation value 1
2010 estimated evaluation value 2
2011 independent condition defining unit
2012 independent condition constant
2013 independent condition constant search unit
2014 disorder priority constant
2015 disorder priority constant search unit
2201 axis of estimated severity of disorder 1
2202 axis of estimated severity of disorder 2
10301 characteristic amount of sample group (1)
10401 characteristic amount of new sample
10501 characteristic amount of sample group (2)
10502 evaluation value of sample group (2)

The invention claimed is:

1. An estimated evaluation value calculation system for calculating an estimated evaluation value from a new subject comprising:
 a measurement device configured to obtain a measurement original data from the new subject;
 a memory configured to store a plurality of pairs of a characteristic amount that is calculated numerically based on the measurement original data each of which was previously measured from a plurality of subjects and an evaluation value that is corresponding to the characteristic amount; and
 a processing device;
 wherein said processing device includes:
 a regression evaluation function calculation unit configured to calculate a regression evaluation function that represents a power of errors between the evaluation value and the estimated evaluation value, based on the plurality of pairs of the characteristic amount and the corresponding the evaluation value stored in said memory
 a discrimination evaluation function calculation unit configured to calculate a discrimination evaluation function that evaluates accuracy of dividing the plurality of pairs of the characteristic amount and the corresponding the evaluation value stored in said memory into a class of an unimpaired group and a class of a patient group depending on each of the characteristic amounts;
 a combination evaluation function calculation unit configured to calculate a combination evaluation function by combining the regression evaluation function and the discrimination evaluation function;
 a combination evaluation function optimization unit configured to calculate a factor of an estimating equation for calculating an estimated evaluation value by optimizing the combination evaluation function;
 a characteristic amount extraction device configured to calculate numerically the measurement original data from said measurement device to obtain a characteristic amount of the new subject;
 an estimating equation application unit configured to calculate the estimated evaluation value by applying a characteristic amount of the new subject to the estimating equation; and
 an output unit configured to output said estimated evaluation value calculated by said estimating equation application unit.

2. The estimated evaluation value calculation system according to claim 1, wherein the combination evaluation function calculation unit comprises a discrimination/regression priority adjusting unit configured to calculate the combination evaluation function by using a predetermined constant that adjusts the priority of the regression evaluation function and the discrimination evaluation function.

3. The estimated evaluation value calculation system according to claim 2, wherein the discrimination/regression priority adjusting unit comprises a priority constant search unit configured to determine the priority constant that optimizes the combination evaluation function.

4. The estimated evaluation value calculation system according to claim 1 comprising:
 an evaluation value substitution table creation unit configured to create a table that associates a numerical value distribution with the evaluation value or associates a numerical value distribution when an evaluation value is absent;
 an evaluation value substitution unit configured to substitute evaluation values of a part of or all of the samples with the numerical value distribution associated by the evaluation value substitution table creation unit, or give evaluation values of a part or all of samples lacking an evaluation value as the numerical value distribution associated by the evaluation value substitution table creation unit; and
 a sample assignment unit configured to assign the sample group, in which the evaluation value is substituted, to the regression evaluation function calculation unit and the discrimination evaluation function calculation unit.

5. The estimated evaluation value calculation system according to claim 4, wherein the numerical value distribution of the evaluation value substitution table creation unit is expressed by a numerical value range which is limited by one or more inequality expression.

6. The estimated evaluation value calculation system according to claim 4, wherein the numerical value distribution of the evaluation value substitution table creation unit is expressed by a numerical value function using the evaluation value as an input.

7. The estimated evaluation value calculation system according to claim 4, wherein the numerical value distribution of the evaluation value substitution table creation unit is a numerical value different from the evaluation value.

8. The estimated evaluation value calculation system according to claim 4, further comprising a convergence determination unit configured to execute a convergence test after the combination evaluation function optimization unit and, when it is not converged, gives feedback to the evaluation value substitution table creation unit to correct the table.

9. The estimated evaluation value calculation system according to claim 1, wherein the regression evaluation function calculated in the regression evaluation function calculation unit is a summation of the power of errors between the evaluation value and estimated evaluation value of the sample group.

10. The estimated evaluation value calculation system according to claim 1, further comprising an important characteristic amount selection unit configured to select a characteristic amount which is closely related to the estimated evaluation value from the characteristic amount.

11. The estimated evaluation value calculation system according to claim 1, further comprising:
- an independent condition defining unit configured to define a condition that a plurality of types of evaluation values are independent from each other;
- and an independent-condition combination evaluation function calculation unit configured to calculate a combination evaluation function with an independent condition by using the independent condition and the combination evaluation function corresponding to a plurality of types of evaluation values.

12. The estimated evaluation value calculation system according to claim 11, wherein the independent condition defining unit configured to define the condition that the two types of evaluation values become independent from each other with a cosine which is obtained by dividing an inner product of axis vectors of the two types of evaluation values by absolute values of the respective axis vectors.

13. The estimated evaluation value calculation system according to claim 11, wherein the independent-condition combination evaluation function calculation unit calculates the combination evaluation function with an independent condition by using an independent condition constant which indicates strength of the independent condition.

14. The estimated evaluation value calculation system according to claim 13, further comprising an independent condition constant search unit configured to search the independent condition constant used in the independent-condition combination evaluation function calculation unit.

15. An estimated evaluation value calculation method for calculating an estimated evaluation value from a new subject comprising:
- measuring, by a measurement device, to obtain a measurement original data from the new subject;
- storing, by a memory, a plurality of pairs of a characteristic amount that is calculated numerically based on the measurement original data each of which was previously measured from a plurality of subjects and an evaluation value that is corresponding to the characteristic amount and
- a processing device;
- wherein said processing device is configured to execute the following steps:
- calculate, by a regression evaluation function calculation unit, a regression evaluation function that represents a power of errors between the evaluation value and the estimated evaluation value, based on the plurality of pairs of the characteristic amount and the corresponding the evaluation value stored in said memory;
- calculate, by a discrimination evaluation function calculation unit, a discrimination evaluation function that evaluates accuracy of dividing the plurality of pairs of the characteristic amount and the corresponding the evaluation value stored in said memory into a class of an unimpaired group and a class of a patient group depending on each of the characteristic amounts;
- calculate, by a combination evaluation function calculation unit, a combination evaluation function by combining the regression evaluation function and the discrimination evaluation function;
- calculate, by a combination evaluation function optimization unit, a factor of an estimating equation for calculating an estimated evaluation value by optimizing the combination evaluation function;
- calculate, by a characteristic amount extraction device, numerically the measurement original data from said measurement device to obtain a characteristic amount of the new subject;
- calculate, by an estimating equation application unit, the estimated evaluation value by applying a characteristic amount of the new subject to the estimating equation; and
- calculate, by an output unit, said estimated evaluation value calculated by said estimating equation application unit.

* * * * *